United States Patent
Pei et al.

(10) Patent No.: US 12,045,219 B2
(45) Date of Patent: Jul. 23, 2024

(54) SCORING METHOD FOR MATCHES BASED ON AGE PROBABILITY

(71) Applicant: Ancestry.com DNA, LLC, Lehi, UT (US)

(72) Inventors: Jingwen Pei, San Mateo, CA (US); Keith D. Noto, San Francisco, CA (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 17/993,370

(22) Filed: Nov. 23, 2022

(65) Prior Publication Data

US 2023/0161749 A1    May 25, 2023

Related U.S. Application Data

(60) Provisional application No. 63/283,044, filed on Nov. 24, 2021.

(51) Int. Cl.
*G06F 16/22* (2019.01)
*G06F 16/2457* (2019.01)
*G06F 16/28* (2019.01)

(52) U.S. Cl.
CPC ...... *G06F 16/2246* (2019.01); *G06F 16/2457* (2019.01); *G06F 16/288* (2019.01)

(58) Field of Classification Search
CPC ...... G06F 16/2246; G06F 16/22; G06F 16/24; G06F 16/2457; G06F 16/288; G16B 20/00; G16B 10/00; G16H 10/20; G16H 50/20; G16H 50/70; G16H 10/60
See application file for complete search history.

(56) References Cited

U.S. PATENT DOCUMENTS

| | | |
|---|---|---|
| 6,277,567 B1 | 8/2001 | Graziosi |
| 6,886,015 B2 | 4/2005 | Notargiacomo et al. |
| 6,950,753 B1 | 9/2005 | Rzhetsky et al. |

(Continued)

OTHER PUBLICATIONS

Browning, S.R. et al., "Rapid and Accurate Haplotype Phasing and Missing-Data Inference for Whole-Genome Association Studies by Use of Localized Haplotype Clustering," The American Journal of Human Genetics, Nov. 2007, pp. 1084-1096, vol. 81.

(Continued)

*Primary Examiner* — Maher N Algibhah
(74) *Attorney, Agent, or Firm* — Fenwick & West LLP

(57) ABSTRACT

Disclosed herein relates to a method that improves the accuracy of producing family trees. The DNA of a target individual is processed to find a matching individual. Using the known family tree of the matching individual, multiple candidate family trees are generated with multiple proposed placements for the target individual. For each candidate family tree, a genetic likelihood for a proposed relationship and the other DNA test takers in the family tree. A birth-year probability is determined by identifying a most recent common ancestor (MRCA). The birth-year probability is based on the number of years between the target individual and the matching individual and a normal distribution of ages for parent-child age differences in a population. The genetic likelihood is converted to a genetic probability so that it can be compared with or added to the birth-year probability. Based on the two probabilities, the candidate family trees are sorted.

20 Claims, 13 Drawing Sheets

(56) References Cited

U.S. PATENT DOCUMENTS

| | | | |
|---|---|---|---|
| 8,185,557 | B2 | 5/2012 | Slinker |
| 8,224,821 | B2 | 7/2012 | Graham et al. |
| 9,116,882 | B1 | 8/2015 | Macpherson et al. |
| 10,957,422 | B2 | 3/2021 | Kermany et al. |
| 2003/0032015 | A1 | 2/2003 | Toivonen et al. |
| 2003/0113756 | A1 | 6/2003 | Mertz |
| 2003/0195707 | A1 | 10/2003 | Schork et al. |
| 2005/0147947 | A1 | 7/2005 | Cookson et al. |
| 2005/0149522 | A1 | 7/2005 | Cookson et al. |
| 2008/0027656 | A1 | 1/2008 | Parida |
| 2008/0081331 | A1 | 4/2008 | Myres et al. |
| 2008/0111716 | A1* | 5/2008 | Artan .................. G06F 21/564 341/50 |
| 2008/0228751 | A1 | 9/2008 | Kenedy et al. |
| 2008/0255768 | A1 | 10/2008 | Martin et al. |
| 2009/0100030 | A1 | 4/2009 | Isakson et al. |
| 2009/0299645 | A1 | 12/2009 | Colby et al. |
| 2010/0218228 | A1 | 8/2010 | Walter |
| 2011/0093448 | A1 | 4/2011 | Rafi et al. |
| 2011/0137944 | A1 | 6/2011 | Rolls |
| 2011/0161168 | A1 | 6/2011 | Dubnicki |
| 2012/0218289 | A1 | 8/2012 | Rasmussen et al. |
| 2013/0149707 | A1 | 6/2013 | Sorenson et al. |
| 2014/0067355 | A1 | 3/2014 | Noto et al. |
| 2014/0278138 | A1 | 9/2014 | Barber et al. |
| 2015/0100243 | A1 | 4/2015 | Myres et al. |
| 2017/0213127 | A1* | 7/2017 | Duncan .................. G16B 50/30 |
| 2020/0058368 | A1* | 2/2020 | Nguyen ................. G16B 25/10 |
| 2020/0118647 | A1* | 4/2020 | Zhang ................... G16B 30/00 |
| 2020/0135296 | A1* | 4/2020 | Girshick ............... G16B 40/20 |
| 2020/0273542 | A1* | 8/2020 | Song ..................... G16B 20/00 |
| 2021/0034647 | A1* | 2/2021 | Nguyen ................. G16H 10/40 |
| 2021/0082167 | A1* | 3/2021 | Jewett .................. G06T 11/001 |
| 2021/0134387 | A1* | 5/2021 | Mcmaster-Schraiber ................... G06N 3/045 |
| 2021/0257060 | A1* | 8/2021 | Curtis ................... G16B 10/00 |

OTHER PUBLICATIONS

Gusev, A. et al., "Whole Population, Genome-Wide Mapping of Hidden Relatedness," Genome Research, Feb. 2009, pp. 318-326, vol. 19.

King, T. et al., "What's in a Name? Y Chromosomes, Surnames and the Genetic Genealogy Revolution," Trends in Genetics, Aug. 2009, pp. 351-360, vol. 25, No. 8.

Noto, K. et al., "Underdog: A Fully-Supervised Phasing Algorithm That Learns from Hundreds of Thousands of Samples and Phases in Minutes," Oct. 20, 2014, 1 page.

Puzzled. "Surnames, 23andMe, and AncestryDNA: Making the Most of Match Counts and 'Enrichment'." Genealogy and Genomics: Genealogy Blog with Attitude, Jan. 25, 2015, 12 pages, [Online] [Retrieved from the Internet Archive dated Apr. 4, 2015], Retrieved from the Internet <URL:http://web.archive.org/web/20150404210843/http://ourpuzzlingpast.com/geneblog/2015/01/25/surnames-23andme-and-ancestrydna-making-the-most-of-match-counts-and-enrichment/>.

Wikipedia. "Identity by Descent." Wikipedia: The Free Encyclopedia, Feb. 13, 2015, 5 pages, [Online] [Retrieved Aug. 3, 2023], Retrieved from the Internet <URL:https://en.wikipedia.org/w/index.php?title=Identity_by_descent&oldid=646873616>.

* cited by examiner

SCORING METHOD FOR MATCHES BASED ON AGE PROBABILITY

CROSS-REFERENCE TO RELATED APPLICATION

The present application claims the benefit of U.S. Provisional Patent Application No. 63/283,044 filed on Nov. 24, 2021, which is hereby incorporated by reference in its entirety.

FIELD

The disclosed embodiments relate to systems, computer program products, and methods for determining and scoring genetic matches.

BACKGROUND

A large-scale database such as user profile and genetic database can include billions of data records, including tens of millions of DNA datasets. This type of database allows users to build family trees, research their family history, and make meaningful discoveries about the lives of their ancestors. Users may try to identify relatives with datasets in the database, for example based on IBD. However, identifying relatives in the vast amount of data is not a trivial task.

Datasets associated with different individuals might never be connected without some determination of a relationship between the datasets. Comparing multiple datasets without a concrete strategy can also be computationally infeasible because each dataset can have a large amount of data bits. Given an individual dataset and a database with datasets that are potentially related to the individual dataset, it is often challenging to identify relationships between the individual dataset and other datasets.

SUMMARY

Various embodiments described herein relate to a computer-implemented method, including: identifying a candidate matching individual using genetic data from a target individual; generating a plurality of candidate family trees based on the genetic data of a target individual and a known family tree of the candidate matching individual, each candidate family tree having a proposed placement of the target individual within the candidate family tree; determining, for each candidate family tree, a genetic likelihood associated with the candidate family tree as depicted by the proposed placement, wherein the genetic likelihood corresponds to a likelihood of a proposed relationship depicted by the proposed placement as opposed to alternative relationships; determining a most recent common ancestor (MRCA) for the target individual and the matching individual; determining, for each candidate family tree, a birth-year probability based on a first number of generations between the target individual and the MRCA and a second number of generations between the matching individual and the MRCA to evaluate the candidate family tree, wherein the birth-year probability is based on a number of years between the target individual and the matching individual and a normal distribution of ages for parent-child age differences in a population; sorting the plurality of candidate family trees based on the genetic likelihood and the birth-year probability in each candidate family tree; and selecting one of the candidate family trees as a proposed family tree.

In some embodiments, the computer-implemented method may further include: removing one or more of the candidate family trees as candidates, wherein the removed candidate family trees are each associated with a value of the birth-year probability that is below a threshold.

In some embodiments, the threshold is 0.01 for one-meiosis-event relationships and two-meiosis-event relationships in order for the one-meiosis-event relationship and the two-meiosis-event relationship to be possible.

In some embodiments, the threshold is 0.1 for three-meiosis-event relationships and more-distant relationships in order for the three-meiosis-event relationships and the more-distant relationships to be possible.

In some embodiments, the computer-implemented method may further include: removing one or more of the candidate family trees as candidates, wherein the removed candidate family trees are associated with duplicate estimates that have equal genetic likelihoods and birth-year probabilities.

In some embodiments, sorting the plurality of candidate family trees is based on the birth-year probability if the genetic probabilities of two candidate family trees are within a similarity threshold.

In some embodiments, sorting the plurality of candidate family trees is first based on genetic likelihoods associated with the plurality of candidate family trees and, secondarily, the birth-year probabilities of the proposed relationships associated with the plurality of candidate family trees.

In some embodiments, the genetic likelihood is converted to the genetic probability using a logarithmic transformation.

In some embodiments, sorting the plurality of candidate family trees includes: determining, for each candidate family tree, a confidence level for the candidate family tree being a correct family tree, wherein the confidence level is determined by summing the birth-year probability and the genetic likelihood; and using the confidence level for each candidate family tree to sort the candidate family trees.

In some embodiments, the determined confidence level is considered high confidence for a candidate family tree that is associated with a one-meiosis-event relationship if the determined confidence level is the highest determined confidence out of determined confidences of the plurality of candidate family trees.

In some embodiments, determining the birth-year probability includes: determining an age difference z between the target individual and the matching individual; determining a first number of generations between the target individual and the MRCA; determining a second number of generations between the matching individual and the MRCA; determining the birth-year probability by determining a cumulative distribution function of the age difference z given the first and second numbers of generations.

In some embodiments, the cumulative distribution function is defined as the age difference z following a relationship N, wherein N is the mean age difference $\mu$ multiplied by the number of generations between the target individual and the MRCA, minus the number of generations between the matching individual and the MRCA, and the standard deviation of the age difference $\sigma$ is multiplied by the square root of the number of generations between the target individual and the MRCA added to the number of generations between the matching individual and the MRCA.

In some embodiments, a non-transitory computer-readable medium that is configured to store instructions is described. The instructions, when executed by one or more processors, cause the one or more processors to perform a process that includes steps described in the above computer-implemented methods or described in any embodiments of this disclosure. In yet another embodiment, a system may include one or more processors and a storage medium that is configured to store instructions. The instructions, when executed by one or more processors, cause the one or more processors to perform a process that includes steps described in the above computer-implemented methods or described in any embodiments of this disclosure.

These and other features of the present disclosure will become better understood regarding the following description, appended claims, and accompanying drawings.

Figure 1:
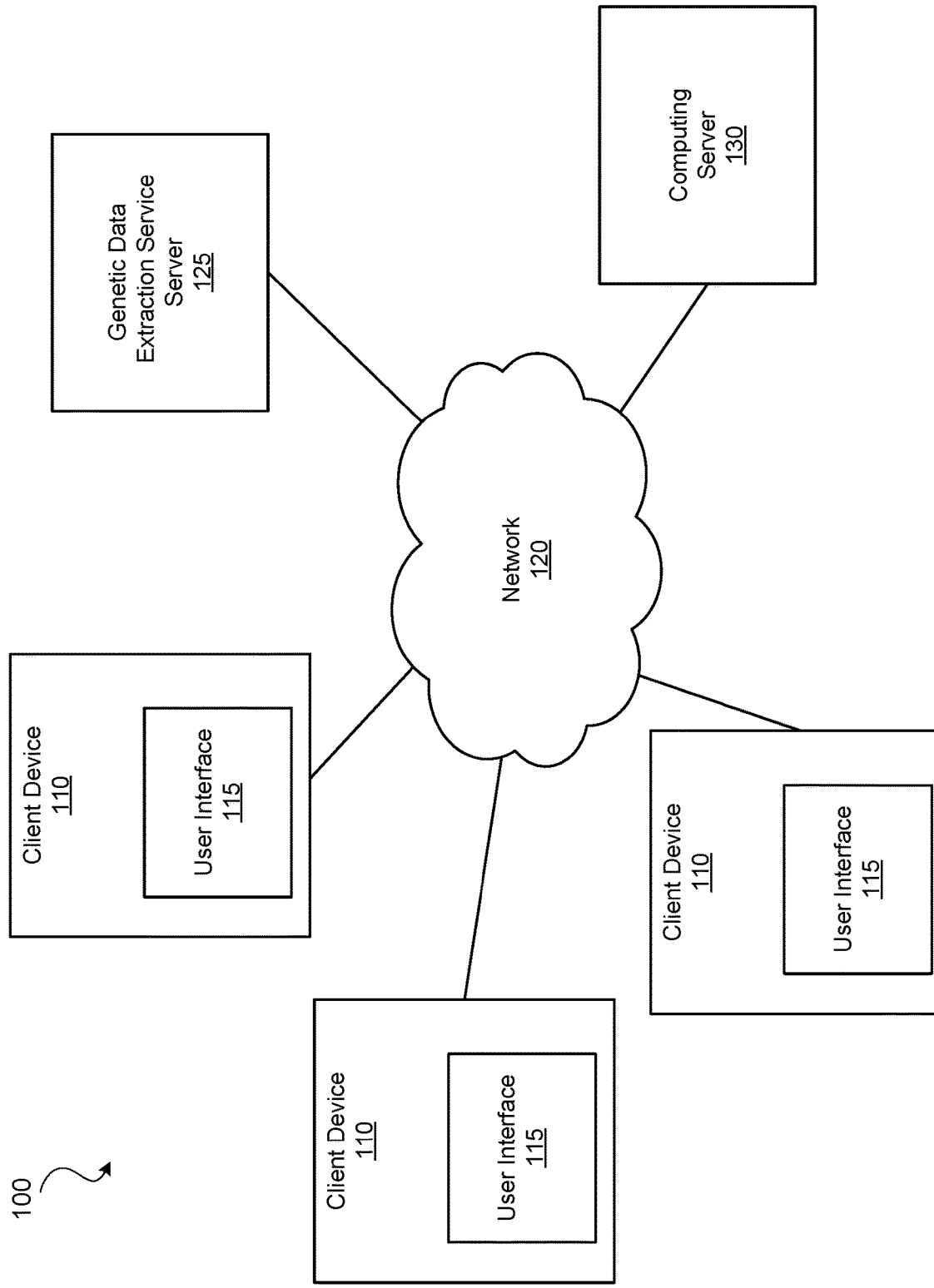
FIG. 1 illustrates a diagram of a system environment of an example computing system, in accordance with some embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures (FIGs.) and the following description relate to preferred embodiments by way of illustration only. One of skill in the art may recognize alternative embodiments of the structures and methods disclosed herein as viable alternatives that may be employed without departing from the principles of what is disclosed.

Introduction

Although the embodiments of the disclosure are adapted for providing genetic match determination and scoring systems and methods in genealogical databases and services, it will be appreciated that the principles of the disclosure may be adapted to any suitable application. Genetic-match determination and/or scoring systems and methods may be provided for users of any genealogical research, DNA test taking, or other service, platform, or application as suitable.

Reference will now be made in detail to several embodiments, examples of which are illustrated in the accompanying figures. It is noted that wherever practicable, similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

In the following description, various examples will be described. For purposes of explanation, specific configurations and details are set forth in order to provide a thorough understanding of the examples. However, it will also be apparent to one skilled in the art that the example may be practiced without the specific details. Furthermore, well-known features may be omitted or simplified in order not to obscure the embodiments being described.

A better understanding of different embodiments of the disclosure may be had from the following description read with the accompanying drawings in which like reference characters refer to like elements. While the disclosure is susceptible to various modifications and alternative constructions, certain illustrative embodiments are in the drawings and are described below. It should be understood, however, there is no intention to limit the disclosure to the embodiments disclosed. On the contrary, the intention covers all modifications, alternative constructions, combinations, and equivalents falling within the spirit and scope of the disclosure. Unless a term is defined in this disclosure to possess a described meaning, there is no intent to limit the meaning of such term, either expressly or indirectly, beyond its plain or ordinary meaning.

Reference characters are provided in the claims for explanatory purposes only and are not intended to limit the scope of the claims or restrict each claim limitation to the element in the drawings and identified by the reference character.

For ease of understanding the disclosed embodiments of a genetic match determination system and method, certain modules and features are described independently. The modules and features may be synergistically combined in some embodiments to provide a genetic match determination system and method.

Overview

Although humans are, genetically speaking, almost entirely identical, small differences in human DNA are responsible for some observed variations between individuals. Most of the mutations that are passed down to descendants are related to single-nucleotide polymorphisms (SNP's). SNP is a substitution of a single nucleotide that occurs at a specific position in the genome. Learning about population structure from genetic polymorphism data is an important topic in genetics.

Identifying segments of identity-by-descent (IBD) matches between pairs of individuals is useful in many applications, so numerous methods have been developed to perform IBD analysis (Purcell et al. 2007, Gusev et al. 2009, Browning and Browning 2011, Browning and Browning 2013). However, these approaches do not scale for continuously growing very large datasets. For example, the existing GERMLINE implementation is designed to take a single input file containing all individuals to be compared against one another. While appropriate for the case in which all samples are genotyped and analyzed simultaneously, this approach is not practical when samples are collected incrementally.

The genomes of individuals who lived long ago can persist in modern populations in the form of genomic segments broken down by recombination and inherited by their descendants. Reconstruction of ancestral genomes, e.g., ancestral chromosomal sequences, using genotype data from a number of their descendants and relatives has been described (Kong et al. (2008) and Meuwissen and Goddard (2010), Elston and Stewart (1971), Lander and Green (1987), Ott (1974); Thompson (2000)). The previous methods require a full family tree or pedigree—i.e., the family tree relationships between all individuals from whom genetic information has been obtained. In addition, previous methods cannot handle large numbers of genotyped descendants or genetic data from hundreds of thousands of genome-wide markers.

Genetic matches determined using IBD or other methods, however, often have limited accuracy in determining a particular relationship. This is a challenge because of the numerous potential relationships at different degrees of separation between individuals. For example, a third cousin once removed, a half third cousin, a half second cousin twice removed, and a second cousin three times removed may all be equally plausible relationships based on a degree of genetic similarity. This range of possibilities limits the usefulness and application of genetic tests.

Embodiments for determining a genetic match according to the present disclosure advantageously allow for improved accuracy in determining genetic matches and/or relationships compared to state-of-the-art methods and systems. In some embodiments, analysis of the birth years for two individuals is used to assess proposed relationships between the individuals.

One individual is a target individual. A target individual is a person who has submitted a genetic data stored in a database and for whom matching individuals are to be automatically identified, according to some embodiments. A matching individual is a person that is determined to be a genetic match to the target individual. According to some embodiments, the genetic match is determined by a number or length of IBD segments. In some embodiments, any genetic relatedness found between the target individual and the matching individual determines a genetic match.

Additionally, a most recent common ancestor (MRCA) of both the target individual and the matching individual is identified using genetic relatedness and genealogical information, according to some embodiments. Genealogical information used to identify a MRCA includes identifying a common ancestor within a family tree of the matching individual and the target individual, according to some embodiments.

Identification of a MRCA using genetic data may be performed according to the methods and components described in U.S. Pat. No. 9,390,225, granted Jul. 12, 2016, U.S. Pat. No. 10,296,710, granted May 21, 2019, U.S. Patent Application Publication No. 2019/0267109, filed May 8, 2019, U.S. Pat. No. 10,504,611, granted Dec. 10, 2019, U.S. Pat. No. 10,679,729, granted Jun. 9, 2020, U.S. Patent Application Publication No. 2020/0098445, filed Dec. 3, 2019, U.S. Patent Application Publication No. 2020/0303035, filed Apr. 29, 2020, each of which is incorporated herein in its entirety by reference.

Variables ($g_i$, $g_j$) may be used to describe the relationship between any given target individual and any given matching individual, according to some embodiments. The variable $g_j$ represents the number of generations from the target individual to an identified MRCA and $g_i$ represents the number of generations from the matching individual to the identified MRCA. The number of generations may be assessed using genealogical data or genetic data, according to some embodiments.

Birth year information is used to augment genetic match data. It has been found that the age difference between two individuals with a parent-child relationship, i.e., a one-generation difference, follows a normal distribution, particularly with a mean difference of 26.5 years and a standard deviation of 7 years for a particular general population.

Given a normal distribution of age differences where the mean age difference in a parent-child relationship is 26.5 years, a relationship (1, 0) (e.g. a relationship where there is one generation between the target individual and MRCA and zero generations between the matching individual and the MRCA) has an age difference which can be characterized by a mean of 26.5 years with a standard deviation of 7. That is, given the relationship ($g_i$, $g_j$) between any given target individual and any given matching individual, the age difference can be represented as following a normal distribution $N$ ($\mu=26.5*(g_i-g_j)$, $\sigma=7*\sqrt{(g_i+g_j)}$).

The target individual is determined to have a birth year of x and the matching individual is determined to have a birth year of y. The age difference between the target individual and the matching individual is defined as the difference between their birth years, (x−y).

A birth-year probability can be represented using P(age difference≥z) by determining the cumulative distribution function (cdf). In an example, a target individual (T) and a matching individual (P) have an age difference x−y=z. Then to test a relationship ($g_i$, $g_j$), the age difference follows $N$ ($\mu=26.5*(g_i-g_j)$, $\sigma=7*\sqrt{(g_i+g_j)}$), as described above.

A probability of the target individual and the matching individual being within a number of generations from each other can then be determined according to Equation (1) below:

$$2*cdf(z) \text{ if } z \leq \mu$$

$$2(cdf(2*(\mu-z))) \text{ if } z < \mu \qquad \text{Eq. 1:}$$

where cdf (z) may be the cumulative distribution function of the normal distribution described above.

Locating a person within an existing family tree may entail a first step of identifying the target individual and identifying a family tree. A candidate family tree is a known family tree modified to propose a relationship between a target individual and a matching individual. In a second step to creating candidate family trees, match information between the target individual and all individuals with genetic data in the family tree are identified. Then every possible way to connect the target individual to the family tree is explored, with genetic likelihood determined for each possibility given match data and tree data. In a third step, the genetic likelihoods are sorted and the scenario with the greatest likelihood is selected. The above steps are described in at least U.S. Pat. No. 11,429,615, granted Aug. 30, 2022, which is incorporated herein in its entirety by reference.

In some embodiments, in an adjustment and augmentation of the second step of the above-mentioned procedure for computing a genetic likelihood for each possibility (i.e. for each possible way to connect or locate a person within a family tree), a birth-year probability is further determined based on match data, tree data, and/or birth year information as described above. A birth-year probability can be determined for each potential placement of the matching individual within the existing family tree.

A scoring strategy may entail, in some embodiments, receiving genetic likelihood and birth-year probability from the augmented second step. Anomaly estimates may be removed using a birth year threshold of, e.g., 0.01. Duplicates may additionally or alternatively be removed. For example, if two estimates have the same genetic likelihood and birth-year probability, they are determined to be identical positions, and one is removed. This reduces the number of possible placement scenarios to be evaluated, improving the performance of a computer-program product or computer system performing an embodiment of the disclosure.

The genetic likelihood may be converted to a probability between 0 and 1, in some embodiments for comparison with a birth-year-based probability. This may be performed by any suitable operation. In an embodiment, the genetic likelihood may be converted to probability using Eq. 2 below, e.g., a logarithmic transformation:

$$p_1 = \frac{e^{x_1}}{e^{x_1} + e^{x_2} + \ldots} \quad \text{Eq. 2}$$

where p1 represents the probability of a particular scenario (e.g. a particular placement within an existing family tree), $x_1$ represents a likelihood of a particular genetic scenario, and $x_2, x_3, \ldots x_n$ represent likelihoods, respectively, of alternative genetic scenarios.

This advantageously allows for direct comparison or summation of genetic probability and birth-year probability. The genetic and birth-year likelihoods are then re-sorted based on probability, for example genetic probability $p_1$, birth-year probability $p_2$, and estimates may be categorized with a confidence level. In some embodiments, the possible arrangements of a target individual within a family tree are sorted first by genetic probability, and to the extent that genetic probabilities are the same or not meaningfully distinguishable, the genetic probabilities are further sorted by birth-year probability.

If the target individual's closest match is M2 or closer, the top estimate may be determined to be "high confidence"; if the target individual's closest match is M3 or M4, the estimate may be determined to be "high confidence" when $p_1+p_2$ is greater than or equal to 1.5, "medium confidence" when $1.5 > p_1+p_2 \geq 1.0$, and "low confidence" when $p_1+p_2 < 1.0$. If the target individual's closest match is M5 or more distant, the estimate may be determined to be "medium confidence" when $p_1+p_2$ is greater than or equal to 0.5 and "low confidence" when $p_1+p_2$ is less than 0.5.

By combining birth year information to yield a birth-year probability, a user, e.g., a target individual, can be connected to and located within a family tree with much greater accuracy. Further, anomaly estimates, such as those with a birth-year probability that is very low, can be easily removed.

Example System Environment

FIG. 1 illustrates a diagram of a system environment 100 of an example computing server 130, in accordance with some embodiments. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliances (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In some embodiments, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more sub-networks, which may include any combination of local area and/or wide area networks, using both wired and/or wireless communication systems. In some embodiments, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. Individuals may also be referred to as users. In some embodiments, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. In some embodiments, a set of SNPs (e.g., 300,000) that are shared between different array platforms (e.g., Illumina OmniExpress Platform and Illumina HumanHap 650Y Platform) may be obtained as genetic data. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms and include information regarding various biomarkers of an individual. For example, in some embodiments, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. A SNP site may also be referred to as a SNP loci. A genetic locus is a segment of a genetic sequence. A locus can be a single site or a longer stretch. The segment can be a single base long or multiple bases long. In some embodiments, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual. SNPs, base pair sequence, genotype, haplotype, RNA sequences, protein sequences, and phenotypes are examples of biomarkers.

The computing server 130 performs various analyses of the genetic data, genealogy data, and users' survey responses to generate results regarding the phenotypes and genealogy of users of computing server 130. Depending on the embodiments, the computing server 130 may also be referred to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnicity compositions of users, paternal and maternal genetic analysis, identification or suggestion of potential family relatives, ancestor information, analyses of DNA data, potential or identified traits such as phenotypes of users (e.g., diseases, appearance traits, other genetic characteristics, and other non-genetic characteristics including social characteristics), etc. The computing server 130 may present or cause the user interface 115 to present the results to the users through a GUI displayed at the client device 110. The results may include graphical elements, textual information, data, charts, and other elements such as family trees.

In some embodiments, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a family tree chart. In some embodiments, subject to user's privacy setting and authorization, the computing server 130 may allow information generated from the user's genetic dataset to be linked to the user profile and to one or more of the family trees. The users may also authorize the computing server 130 to analyze their genetic dataset and allow their profiles to be discovered by other users.

Example Computing Server Architecture

Figure 2:
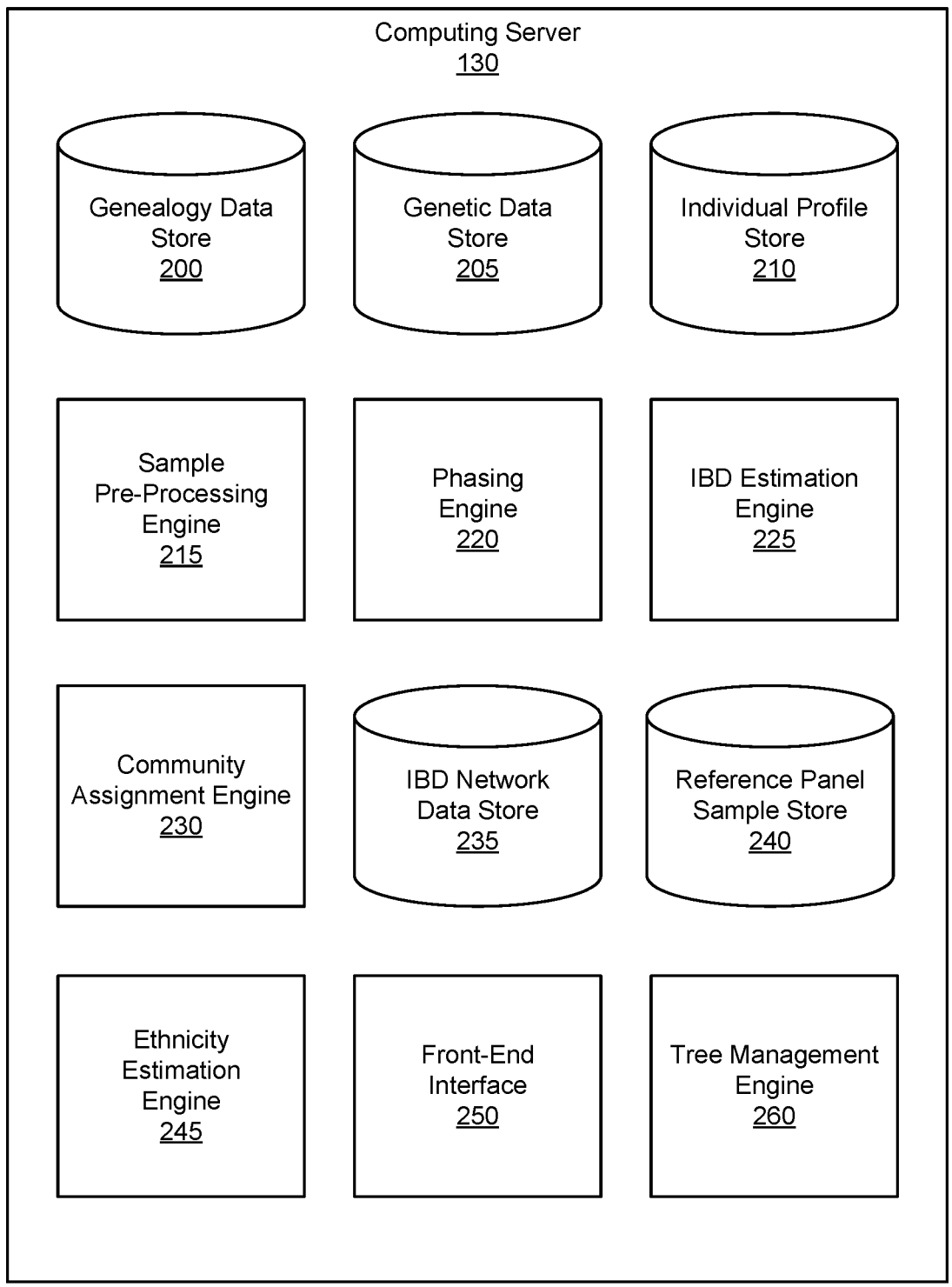
FIG. 2 is a block diagram of an architecture of an example computing system, in accordance with some embodiments.

FIG. 2 is a block diagram of an architecture of an example computing server 130, in accordance with some embodiments. In the embodiment shown in FIG. 2, the computing server 130 includes a genealogy data store 200, a genetic data store 205, an individual profile store 210, a sample pre-processing engine 215, a phasing engine 220, an identity by descent (IBD) estimation engine 225, a community assignment engine 230, an IBD network data store 235, a reference panel sample store 240, an ethnicity estimation engine 245, a front-end interface 250, and a tree management engine 260. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogy data, and survey response data. The computing server 130 processes the genetic data of users to identify shared identity-by-descent (IBD) segments between individuals. The genealogy data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to the basic information of the user (e.g., name, date of birth, birthplace, etc.) and later on more advanced questions that may be useful for obtaining additional genealogy data. The computing server 130 may also include survey questions regarding various traits of the users such as the users' phenotypes, characteristics, preferences, habits, lifestyle, environment, etc.

Genealogy data may be stored in the genealogy data store 200 and may include various types of data that are related to tracing family relatives of users. Examples of genealogy data include names (first, last, middle, suffixes), gender, birth locations, date of birth, date of death, marriage information, spouse's information kinships, family history, dates and places for life events (e.g., birth and death), other vital data, and the like. In some instances, family history can take the form of a family tree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, and offspring in some cases. Genealogy data may also include connections and relationships among users of the computing server 130. The information related to the connections among a user and her relatives that may be associated with a family tree may also be referred to as family tree data or family tree data.

In addition to user-input data, genealogy data may also take other forms that are obtained from various sources such as public records and third-party data collectors. For example, genealogical records from public sources include birth records, marriage records, death records, census records, court records, probate records, adoption records, obituary records, etc. Likewise, genealogy data may include data from one or more family trees of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogy data store 200 may also include relationship information inferred from the genetic data stored in the genetic data store 205 and information received from the individuals. For example, the relationship information may indicate which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data (e.g., SNP data) and corresponding metadata. A genetic dataset may contain data on the whole or portions of an individual's genome. The genetic data store 205 may store a pointer to a location associated with the genealogy data store 200 associated with the individual. A genetic dataset may take different forms. In some embodiments, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP loci (e.g., allele sites) filtered from the sequencing results. A SNP locus that is single base pair long may also be referred to a SNP site. A SNP locus may be associated with a unique identifier. The genetic dataset may be in a form of diploid data that includes a sequencing of genotypes, such as genotypes at the target SNP loci, or the whole base pair sequence that includes genotypes at known SNP loci and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual. In other contexts, a genotype may be a pair of alleles present on two chromosomes for an individual at a given genetic marker such as a SNP site.

Genotype data for a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 210 stores profiles and related metadata associated with various individuals appeared in the computing server 130. A computing server 130 may use unique individual identifiers to identify various users and other non-users that might appear in other data sources such as ancestors or historical persons who appear in any family tree or genealogy database. A unique individual identifier may be a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointers associating genetic datasets such as genotype and phased haplotype data of the individual that are saved in the genetic data store 205. The metadata about the individual may also be individual information related to family trees and family tree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, or preferences, location and the like. In some embodiments, the user profile data may also include one or more photos of the users and photos of relatives (e.g., ancestors) of the users that are uploaded by the users. A user may authorize the computing server 130 to analyze one or more photos to extract information, such as the user's or relative's appearance traits (e.g., blue eyes, curved hair, etc.), from the photos. The appearance traits and other information extracted from the photos may also be saved in the profile store. In some cases, the computing server may allow users to upload many different photos of the users, their relatives, and even friends. User profile data may also be obtained from other suitable sources, including historical records (e.g., records related to an ancestor), medical records, military records, photographs, other records indicating one or more traits, and other suitable recorded data.

For example, the computing server 130 may present various survey questions to its users from time to time. The responses to the survey questions may be stored at individual profile store 210. The survey questions may be related to various aspects of the users and the users' families. Some survey questions may be related to users' phenotypes, while other questions may be related to environmental factors of the users.

Survey questions may concern health or disease-related phenotypes, such as questions related to the presence or absence of genetic diseases or disorders, inheritable diseases or disorders, or other common diseases or disorders that have a family history as one of the risk factors, questions regarding any diagnosis of increased risk of any diseases or disorders, and questions concerning wellness-related issues such as a family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's disease, diabetes, cancer, and obesity. The computing server 130 may obtain data on a user's disease-related phenotypes from survey questions about the health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as the ability to sense an asparagus metabolite. Traits may also be collected from historical records, electronic health records and electronic medical records.

The computing server 130 also may present various survey questions related to the environmental factors of users. In this context, an environmental factor may be a factor that is not directly connected to the genetics of the users. Environmental factors may include users' preferences, habits, and lifestyles. For example, a survey regarding users' preferences may include questions related to things and activities that users like or dislike, such as types of music a user enjoys, dancing preference, party-going preference, certain sports that a user plays, video game preferences, etc. Other questions may be related to the users' diet preferences such as like or dislike a certain type of food (e.g., ice cream, egg). A survey related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g. stretching, flexibility, heart rate recovery), family type (adopted family or not, has siblings or not, lived with extended family during childhood), property and item ownership (has home or rents, has a smartphone or doesn't, has a car or doesn't).

Surveys also may be related to other environmental factors such as geographical, social-economic, or cultural factors. Geographical questions may include questions related to the birth location, family migration history, town, or city of users' current or past residence. Social-economic questions may be related to users' education level, income, occupations, self-identified demographic groups, etc. Questions related to culture may concern users' native language, language spoken at home, customs, dietary practices, etc. Other questions related to users' cultural and behavioral questions are also possible.

For any survey questions asked, the computing server 130 may also ask an individual the same or similar questions regarding the traits and environmental factors of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogy data store 200 and genetic data store 205.

The user profile data, photos of users, survey response data, the genetic data, and the genealogy data may be subject to the privacy and authorization setting of the users to specify any data related to the users that can be accessed, stored, obtained, or otherwise used. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user profile data, photos, genetic data, and other sensitive data. For example, the user may pre-authorize the access to the data and may change the setting as wished. The privacy settings also may allow a user to specify (e.g., by opting out, by not opting in) whether the computing server 130 may receive, collect, log, or store particular data associated with the user for any purpose. A user may restrict her data at various levels. For example, on one level, the data may not be accessed by the computing server 130 for purposes other than displaying the data in the user's own profile. On another level, the user may authorize anonymization of her data and participate in studies and researches conducted by the computing server 130 such as a large-scale genetic study. On yet another level, the user may turn some portions of her genealogy data public to allow the user to be discovered by other users (e.g., potential relatives) and be connected to one or more family trees. Access or sharing of any information or data in the computing server 130 may also be subject to one or more similar privacy policies. A user's data and content objects in the computing server 130 may also be associated with different levels of restriction. The computing server 130 may also provide various notification features to inform and remind users of their privacy and access settings. For example, when privacy settings for a data entry allow a particular user or other entities to access the data, the data may be described as being "visible," "public," or other suitable labels, contrary to a "private" label.

In some cases, the computing server 130 may have a heightened privacy protection on certain types of data and data related to certain vulnerable groups. In some cases, the heightened privacy settings may strictly prohibit the use, analysis, and sharing of data related to a certain vulnerable group. In other cases, the heightened privacy settings may specify that data subject to those settings require prior approval for access, publication, or other use. In some cases, the computing server 130 may provide the heightened privacy as a default setting for certain types of data, such as genetic data or any data that the user marks as sensitive. The user may opt in to sharing of those data or change the default privacy settings. In other cases, the heightened privacy settings may apply across the board for all data of certain groups of users. For example, if computing server 130 determines that the user is a minor or has recognized that a picture of a minor is uploaded, the computing server 130 may designate all profile data associated with the minor as sensitive. In those cases, the computing server 130 may have one or more extra steps in seeking and confirming any sharing or use of the sensitive data.

The sample pre-processing engine 215 receives and pre-processes data received from various sources to change the data into a format used by the computing server 130. For genealogy data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogy data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. In some embodiments, the SNPs may be autosomal SNPs. In some embodiments, 700,000 SNPs may be identified in an individual's data and may be stored in genetic data store 205. Alternatively, in some embodiments, a genetic dataset may include at least 10,000 SNP sites. In another embodiment, a genetic dataset may include at least 100,000 SNP sites. In yet another embodiment, a genetic dataset may include at least 300,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP locus of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

By way of example, the phasing engine 220 may use a directed acyclic graph model such as a hidden Markov model (HMM) to perform the phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. Pat. No. 10,679,729, entitled "Haplotype Phasing Models," granted on Jun. 9, 2020, describes example embodiments of haplotype phasing. Other example phasing embodiments are described in U.S. Patent Application Publication No. US 2021/0034647, entitled "Clustering of Matched Segments to Determine Linkage of Dataset in a Database," published on Feb. 4, 2021.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicates the mismatch is not attributable to potential errors in phasing or imputation. The IBD estimation engine 225 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 130 may save data regarding individual pairs who share a length of IBD segments exceeding a predetermined threshold (e.g., 6 cM), in a suitable data store such as in the genealogy data store 200. U.S. Pat. No. 10,114,922, entitled "Identifying Ancestral Relationships Using a Continuous stream of Input," granted on Oct. 30, 2018, and U.S. Pat. No. 10,720,229, entitled "Reducing Error in Predicted Genetic Relationships," granted on Jul. 21, 2020, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 230 assigns individuals to one or more genetic communities based on the genetic data of the individuals. A genetic community may correspond to an ethnic origin or a group of people descended from a common ancestor. The granularity of genetic community classification may vary depending on embodiments and methods used to assign communities. For example, in some embodiments, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., the Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. Pat. No. 10,223,498, entitled "Discovering Population Structure from Patterns of Identity-By-Descent," granted on Mar. 5, 2019, describes example embodiments of community detection and assignment.

The community assignment engine 230 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. A reference panel sample is a genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, determining the ethnic composition of an individual, and determining the accuracy of any genetic data analysis, such as by computing a posterior probability of a classification result from a classifier.

A reference panel sample may be identified in different ways. In some embodiments, an unsupervised approach in community detection may apply the clustering algorithm recursively for each identified cluster until the sub-clusters contain a number of nodes that are smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of the times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected. For example, a candidate reference panel sample may be selected from an individual whose recent ancestors are born at a certain birthplace. The computing server 130 may also draw sequence data from the Human Genome Diversity Project (HGDP). Various candidates may be manually screened based on their family trees, relatives' birth location, and other quality control. Principal component analysis may be used to create clusters of genetic data of the candidates. Each cluster may represent an ethnicity. The predictions of the ethnicity of those candidates may be compared to the ethnicity information provided by the candidates to perform further screening.

The ethnicity estimation engine 245 estimates the ethnicity composition of a genetic dataset of a target individual. The genetic datasets used by the ethnicity estimation engine 245 may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In some embodiments, the ethnicity estimation engine 245 divides a target genetic dataset into a plurality of windows (e.g., about 1000 windows). Each window includes a small number of SNPs (e.g., 300 SNPs). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of node groups. Each node group, representing a window, includes a plurality of nodes. The nodes represent different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverse the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 245 determines the emission probabilities by comparing SNPs in the window corresponding to the target genetic dataset to corresponding SNPs in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. Pat. No. 10,558,930, entitled "Local Genetic Ethnicity Determination System," granted on Feb. 11, 2020 and U.S. Pat. No. 10,692,587, granted on Jun. 23, 2020, entitled "Global Ancestry Determination System" describe different example embodiments of ethnicity estimation.

The front-end interface 250 displays various results determined by the computing server 130. The results and data may include the IBD affinity between a user and another individual, the community assignment of the user, the ethnicity estimation of the user, phenotype prediction and evaluation, genealogy data search, family tree and family tree, relative profile and other information. The front-end interface 250 may allow users to manage their profile and data trees (e.g., family trees). The users may view various public family trees stored in the computing server 130 and search for individuals and their genealogy data via the front-end interface 250. The computing server 130 may suggest or allow the user to manually review and select potentially related individuals (e.g., relatives, ancestors, close family members) to add to the user's data tree. The front-end interface 250 may be a graphical user interface (GUI) that displays various information and graphical elements. The front-end interface 250 may take different forms. In one case, the front-end interface 250 may be a software application that can be displayed on an electronic device such as a computer or a smartphone. The software application may be developed by the entity controlling the computing server 130 and be downloaded and installed on the client device 110. In another case, the front-end interface 250 may take the form of a webpage interface of the computing server 130 that allows users to access their family tree and genetic analysis results through web browsers. In yet another case, the front-end interface 250 may provide an application program interface (API).

The tree management engine 260 performs computations and other processes related to users' management of their data trees such as family trees. The tree management engine 260 may allow a user to build a data tree from scratch or to link the user to existing data trees. In some embodiments, the tree management engine 260 may suggest a connection between a target individual and a family tree that exists in the family tree database by identifying potential family trees for the target individual and identifying one or more most probable positions in a potential family tree. A user (target individual) may wish to identify family trees to which he or she may potentially belong. Linking a user to a family tree or building a family may be performed automatically, manually, or using techniques with a combination of both. In an embodiment of an automatic tree matching, the tree management engine 260 may receive a genetic dataset from the target individual as input and search related individuals that are IBD-related to the target individual. The tree management engine 260 may identify common ancestors. Each common ancestor may be common to the target individual and one of the related individuals. The tree management engine 260 may in turn output potential family trees to which the target individual may belong by retrieving family trees that include a common ancestor and an individual who is IBD-related to the target individual. The tree management engine 260 may further identify one or more probable positions in one of the potential family trees based on information associated with matched genetic data between the target individual and those in the potential family trees through one or more machine learning models or other heuristic algorithms. For example, the tree management engine 260 may try putting the target individual in various possible locations in the family tree and determine the highest probability position(s) based on the genetic datasets of the target individual and other members in the family tree and based on genealogy data available to the tree management engine 260. The tree management engine 260 may provide one or more family trees from which the target individual may select. For a suggested family tree, the tree management engine 260 may also provide information on how the target individual is related to other individuals in the tree. In a manual tree building, a user may browse through public family trees and public individual entries in the genealogy data store 200 and individual profile store 210 to look for potential relatives that can be added to the user's family tree. The tree management engine 260 may automatically search, rank, and suggest individuals for the user conduct manual reviews as the user makes progress in the front-end interface 250 in building the family tree.

As used herein, "pedigree" and "family tree" may be interchangeable and may refer to a family tree chart or pedigree chart that shows, diagrammatically, family information, such as family history information, including parentage, offspring, spouses, siblings, or otherwise for any suitable number of generations and/or people, and/or data pertaining to persons represented in the chart. U.S. Patent Publication Application No., entitled "Linking Individual Datasets to a Database," US2021/0216556, published on Jul. 15, 2021, describes example embodiments of how an individual may be linked to existing family trees.

Embodiments of Genetic-Match Determination and Scoring

Embodiments described herein related to genetic-match determination and scoring systems and methods that address shortcomings in the art by facilitating improved accuracy when determining a genetic match of a target individual and identifying a relevant family tree for the target individual. For example, a relationship between a target individual and a matching individual may be more accurately provided with or located within a family tree by augmenting genetic match information with birth-year information. Additionally or alternatively, an identified genetic match may be scored in a novel and improved way.

In some embodiments, the process of determining genetic match includes identifying a most-recent common ancestor (MRCA) common to a target individual and a matching individual. A birth year of both a target individual and a matching individual may be obtained from family tree data, such as one obtainable from a stitched tree database. The MRCA may be obtained by comparing family trees obtained from the stitched tree database. Candidate family tree(s) placing the target individual (who may not have a family tree) within an existing family tree of the matching individual are proposed and ranked based on a likelihood of accuracy. Stitched tree databases are described in at least U.S. Patent Application Publication No. 2020/0394188, published on Dec. 17, 2020, and U.S. Pat. No. 11,347,798, granted on May 31, 2022, each of which is incorporated herein in its entirety by reference.

Figure 3:
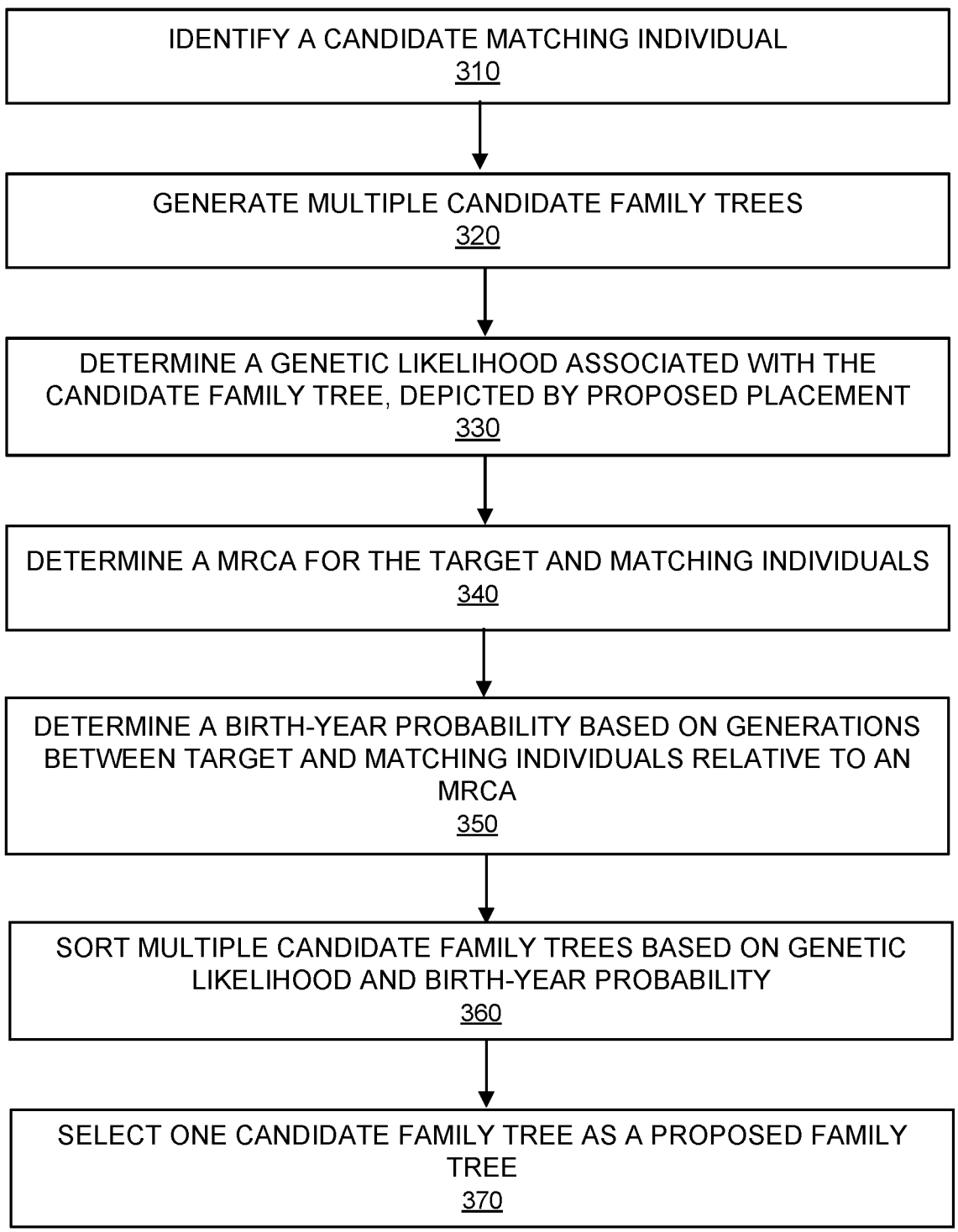
FIG. 3 is a flowchart depicting a example process for determining confidence levels of multiple proposed candidate family trees.

FIG. 3 is a flowchart depicting an example process 300 for determining and scoring a genetic match, in accordance with some embodiments. The process may be performed by computing devices such as the computing server 130. For example, the tree management engine 260 may use the process 300 to suggest one or more proposed family trees or family tree placement to a user. The process 300 may be embodied as a software algorithm that may be stored as computer instructions that are executable by one or more processors. The instructions, when executed by the processors, cause the processors to perform various steps in the process 300. In various embodiments, the process may include additional, fewer, or different steps in any suitable orders. While various steps in process 300 may be discussed with the use of computing server 130, each step may be performed by a different computing device.

The process 300 includes a step 310 of identifying a candidate matching individual based on processing a DNA sample of a target individual, according to some embodiments. In some embodiments, a target individual is a person that has genetic data stored in the computing server 130. The target individual may or may not have a family tree (e.g., a new user) stored on the computing server 130. In some embodiments, the target individual may submit a DNA sample that is processed to be genetic data or the computing server 130 may otherwise acquire the genetic data of the target individual. The genetic data is processed by performing IBD analysis with regard to existing genetic data of various individuals stored in the computing server 130, such as by using the phasing engine 220 and IBD estimation engine 225. The IBD estimation engine 225 may identify potential genetics matches of the target individual. Identifying potential genetic matches includes identifying a possible relationship between the matches based on factors including, but not limited to, number of centimorgans ("cM") shared, number of segments shared, etc. Those matches may be referred to as IBD matches. Detail of identifying a matching individual using the IBD estimation engine 225 is further described in regards to FIG. 2. For the purpose of the process 300, a matching individual at this stage may be referred to as a candidate matching individual because the predicted relationship between the target individual and the candidate match person are further evaluated in the process 300.

Among the potential genetic matches, a close match (such as the closest match) may be further analyzed. An example of a close match may be a third cousin. The computing server 130 may identify a close match who is associated with a family tree stored in the computing server 130. The computing server 130 may retrieve the associated family tree. The family tree contains one or more nodes (representing persons) connected by edges (representing relationships between the persons). In some embodiments, one or more nodes of the retrieved family tree that have associated genetic data are identified. Such steps are described in at least U.S. Pat. No. 11,429,615, granted Aug. 30, 2022, and incorporated herein in its entirety by reference.

With continued reference to FIG. 3, the process 300 can additionally include a step 320 of generating one or more candidate family trees based on the genetic data of the target individual and an existing family tree, such as a family tree of the matching individual. Each candidate family tree proposes a placement for the target individual in relation to the other individuals in the family tree. The existing family tree may be a family tree identified from a stitched tree database.

One or more candidate family trees are generated using predicted relationships. For example, a target individual named Tom may have, as a closest relative in the databases of the computing server 130, a third cousin named Nancy. Nancy has a family tree including her parents, two brothers, and one brother's spouse and child named Jason. The brother's spouse and Jason also have genetic data stored in the computing server 130. One candidate family tree attempts to locate the target individual Tom as a child of Nancy's other brother. Another candidate family tree attempts to locate Tom as a child of Jason, and so on, producing a plurality of candidate family trees.

By way of example, the tree management engine 260 may use various operations such as replacing, splitting, and extending to propose different placements of the target individual in the existing family tree. U.S. Pat. No. 11,429,615, entitled "Linking Individual Datasets to a Database," granted Aug. 30, 2022, describes various operations of how a target individual may be placed.

With continued reference to FIG. 3, the process 300 can additionally include a step 330 of determining a genetic likelihood of a candidate family tree based on the determined relationships between family members within the family tree who have genetic data and the target individual based on the proposed placement of the target individual within the candidate family tree. The step 330 may be repeated for the various candidate family members with different proposed placements of the target individual to determine the genetic likelihood for each candidate family tree.

In some embodiments, the genetic likelihood of a candidate family tree may be a composite likelihood score that is determined based on the genetic likelihoods of various relationships in the candidate family tree. By way of example, for each candidate family tree, a genetic likelihood is determined based on a relationship between each pair of family members in the family tree who have genetic data stored in the computing server 130. The genetic likelihood of the candidate family tree may be an aggregate of various known relationships, e.g., 3rd cousins, 4th-6th cousins, no relationship between certain people, etc. The genetic likelihood may also be based on the relationships between the target individual and other family members based on the proposed placement. The determination of genetic likelihood may be repeated for other matches to a target individual.

For each candidate tree, a composite likelihood score may be calculated based on genetic data and genealogical data associated with the target individual and candidate matches in the candidate tree. Calculation with regard to composite likelihood is discussed in further detail below.

In some embodiments, the likelihood of the relationship between two individuals i and j is calculated based on observed IBD $L_{ij}$ such as length or number of segments of IBD between individuals i and j. The relationship between individuals i and j may be referred to as $g=(g_i, g_j)$. Suppose the candidate family tree includes M candidate matches, the full likelihood of the IBD sharing may be approximated to be a product of pairwise sharing between the target individual and all other candidates in the candidate family tree, that is, M pairs of individuals in the network. Therefore, it is necessary to obtain a way of calculating the likelihood of the relationship $g_i$, $g_j$ between two individuals i, j for observed IBD $L_{ij}$ For ease of notation, the likelihood is expressed as $L(g)=P(L_{ij}|g)$, which may be used as a building block for the composite likelihood.

The first step is to model the length of an IBD segment shared by two related individuals given that the two individuals find a most recent common ancestor (MRCA) at g generations in the past. For a pair of individuals i and j, assume that they do not have more than a single individual or couple that is a recent common ancestor (CA) between (i.e. no inbreeding). Suppose that these individuals find a common ancestor at $g_i$, $g_j$ generations back from their own generation, respectively. With the exception of full siblings (with two IBD sharing segments which violates assumptions), at a given site in the genome, the density of IBD length l (in centimorgans) is given by:

$$p(l \mid g_i, g_j) = \begin{cases} 2^{-g_i-g_j+1+\delta(i,j)}\left(\frac{g_i+g_j}{100}\right)^2 le^{-\frac{g_i+g_j}{100}l}, & \text{if } l > 0 \\ 1-2^{-g_i-g_j+1+\delta(i,j)}, & \text{if } l = 0 \end{cases} \text{ where,}$$

-continued $$\delta(i, j) = \begin{cases} 0, & \text{if } CA(i, j) \text{ is an individual} \\ 1, & \text{if } CA(i, j) \text{ is a couple} \end{cases}$$

Therefore, $\delta(i, j)=0$ is equivalent to one of the two cases: 1) i and j are half-relatives, or 2) i is an ancestor of j or vise-versa. For example, if i is the parent of j, then $\delta(i, j)=0$.

Note that the segment length is conditional on the length being nonzero (i.e. $p(l|l>0, g_i, g_j)$) and has an Erlang-2 distribution. That is, it takes the distribution of the sum of two exponential random variables, each corresponding to the closest recombination breakpoint to the site of interest that has occurred throughout all meiosis between i and j. Specifically, the distribution is equivalent to the distribution of $X_1+X_2$, where $X_1$ and $X_2$ are independent identical distribution (iid) of $$\text{Exp}\left(\frac{g_i + g_j}{100}\right),$$

which may be considered as the distribution of the sum of the minimums of two iid vectors of iid Exp(100) variables with one vector of length $g_i$ and the other vector of length $g_j$. Intuitively, the greater the value of g, the more likely the IBD is split into a smaller piece.

The second step is to model the spectrum of IBD segments shared by two related individuals. For some observed spectrum of n IBD segments $L=(L_1, L_2, \ldots, L_n)$ shared between i and j, it is assumed that the likelihood for $g=(g_i, g_j)$ is:

$$L(g) = \begin{cases} P(N = n | g) \prod_{k=1}^{n} q(l_k | g), & \text{if } n > 0 \\ P(N = 0 | g), & \text{if } n = 0 \end{cases}$$

It is presumed that given the number of IBD segments, the lengths are conditionally independent of one another and are identically distributed.

Note that the distribution q in the product is a different distribution than the distribution p discussed above. The distribution q may be perceived as the length-normalized distribution of segments, that is, conditioning on any arbitrary N=n, q is the distribution of how frequent a single segment of length l is among those n segments of varying length. The distribution of q is derived as:

$$q(l | g) = \frac{p(l | g)}{l} \bigg/ \int_0^{+\infty} \frac{p(l | g)}{l} dl = \frac{g_i + g_j}{100} e^{-\frac{g_i + g_j}{100} l}$$

As a result from the modeling, the number of segments and the total IBD length are sufficient to infer g, that is:

$$L(g) = P(N = n | g) \prod_{k=1}^{n} q(l_k | g) = P(N = n | g) \left(\frac{g_i + g_j}{100}\right)^n e^{-\frac{g_i + g_j}{100} \Sigma_k l_k}$$

This proves that for most pairwise relationships, the number and the total length of the IBD segments are sufficient to infer the underlying relationship g.

In practice, it is useful to just examine IBD segments that are thresholded below by a certain u>0. In such case, the distribution of q is derived as:

$$q_u(l | g) = \frac{p(l | g)}{l} \bigg/ \int_u^{+\infty} \frac{p(l | g)}{l} dl$$

For l>u, the distribution of $q_u$ is proportional to the original q. For example, a threshold u=5 is used in the analysis.

The number of IBD segments (thresholded by u) is modeled as a Poisson random variable with rate parameter $\lambda$, with $$\lambda = \frac{\gamma}{100} 2^{-g+1+\delta(i,j)} g e^{-\frac{u}{100}g},$$

where $\gamma$ is genome length in cM.

If no recent common ancestor information is known, the approach is to integrate over all possible generations at which the two individuals could share a CA, and the probability of waiting t generations to find a common ancestor is modeled as a geometric distribution with success rate $$\frac{1}{N_e}$$

where $N_e$ is the elective population size. The segment length distribution is modeled as $$p_{bkgd}(l) = \frac{2N_e(50 + N_e \times \mu)^2}{(50 + l \times N_e)^3}.$$

The number of IBD segments as a Poisson random variable with rate parameter $$\lambda_{bkgd} = \frac{\gamma \times 50 \times N_e}{(50 + N_e \times \mu)^2}.$$

To compute the composite likelihood for a candidate family tree based on observed IBD segments, consider the individuals in a candidate family tree of with genetic data and assume the number of such individuals is M. Each pair of individuals i and j in the candidate family tree has $g_i$ and $g_j$ number of generations to the most recent common ancestor (CA). For ease of notation, $g=(g_i, g_j)$. Let $l^{(ij)}$ denote the observed spectrum of IBD segments between the pair of individuals i and j. For the case when there is no IBD sharing, denote $l^{(ij)}=\{\emptyset\}$. Let the number of segments $n_{ij}=|l^{(ij)}|$. The composite likelihood of $g:=(g_{ij})_{i \neq j}$ is given by:

$$CL(g) = \prod_{i \neq j} P\left(L^{(ij)} | g_{ij}\right)^{\frac{1}{M-1}} = \prod_{i \neq j} \left[P(N = n_{ij} | g_{ij}) \prod_{k=1}^{n_{ij}} q(l_k^{(ij)} | g_{ij})\right]^{\frac{1}{M-1}}$$

Intuitively, the equation above determines a likelihood for each pair of individuals i and j in the candidate family tree and generates a composite likelihood by multiplying the likelihood for each pair of individuals. The likelihood for each pair of individuals indicates a probability that individuals i and j have $g_i$ and $g_j$ generations away from the common ancestor respectively based on observed IBD segments (e.g., matched DNA data bits). The composite likelihood is determined based on a product of the likelihood for each pair of individuals in the candidate data tree.

In some embodiments, in addition to determining the genetic likelihood, the process 300 may include converting a genetic likelihood to a probability, using Eq. 2 herein:

$$p = \frac{e^{x_1}}{e^{x_1} + e^{x_2} + \ldots} \qquad \text{Eq. 2}$$

Converting the genetic likelihood to a genetic probability allows for a normalization of the genetic and birth-year probabilities for comparison. Comparison can of the birth-year probabilities and genetic likelihoods can be done by summation or other calculations. The determination of a birth-year probability is discussed in step 350.

With continued reference to FIG. 3, the process 300 can additionally include a step 340 of determining an MRCA for the target individual and the candidate matching individual. Identification of a MRCA using genetic data may be performed according to the methods and components described in U.S. Pat. No. 9,390,225, granted Jul. 12, 2016, U.S. Pat. No. 10,296,710, granted May 21, 2019, U.S. Patent Application Publication No. 2019/0267109, filed May 8, 2019, U.S. Pat. No. 10,504,611, granted Dec. 10, 2019, U.S. Pat. No. 10,679,729, granted Jun. 9, 2020, U.S. Patent Application Publication No. 2020/0098445, filed Dec. 3, 2019, U.S. Patent Application Publication No. 2020/0303035, filed Apr. 29, 2020, each of which is incorporated herein in its entirety by reference.

With continued reference to FIG. 3, the process 300 can additionally include a step 350 of determining a birth-year probability using identified generations between a target individual and a match person relative to the identified MRCA. In order to determine the birth-year probability, a distribution of age differences in a general population may be used as the underlying distribution.

Figure 4:
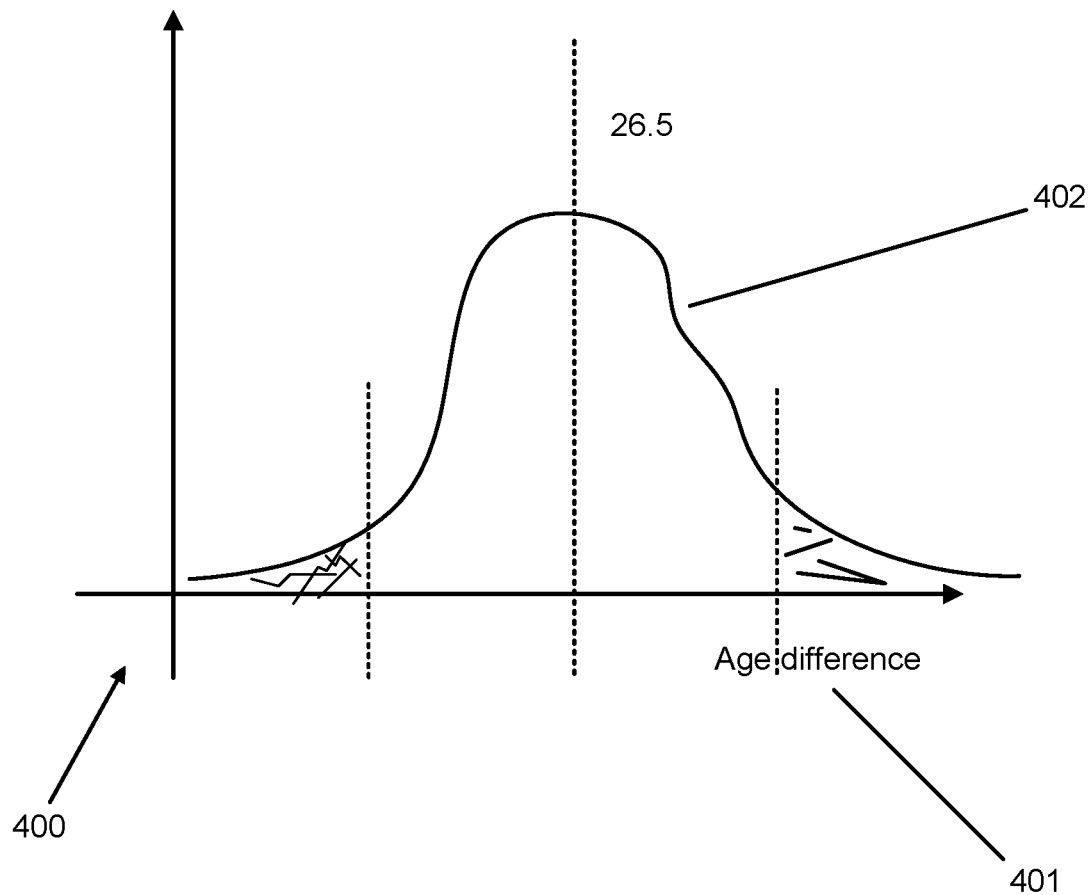
FIG. 4 is graph of the normal distribution of age difference for a one-meiosis-event relationship, according to some embodiments.

Temporarily referring to FIG. 4, FIG. 4 is a conceptual diagram illustrating a normal distribution of age differences 401 that shows the user of age differences to augment estimates based on genetic data improves the accuracy in predicting and scoring proposed relationship between two persons, in accordance with some embodiments. It has been found that age differences 301 between parent-child relationships in a general population may follow a normal distribution 302 with a mean of 26.5 years and a standard deviation of 7 years. This distribution is an example distribution only and the distribution may change based on demographics, generations, time, and other factors. The normal distribution of age differences for some embodiments includes that a relationship (1, 0) has an age difference $N$ ($\mu=26.5$, $\sigma=7$). In such an embodiment, given a relationship ($g_i$, $g_j$), the age difference follows the normal distribution $N$ ($\mu=26.5*(g_i-g_j)$, $\sigma=7*\sqrt{(gi+gj)}$).

The birth-year probability can be represented using P(age difference≥z) using a cumulative distribution function (CDF). In an example, a target individual ("T") and a candidate matching individual ("P") have an age difference x−y=z. To test a relationship (gi, gj), the age difference follows $N$ ($\mu=26.5*(g_i-g_j)$, $\sigma=7*\sqrt{(gi+gj)}$).

In some embodiments, a birth-year probability may be determined according to equation (1) as described herein:

$$2*cdf(z) \text{ if } z \leq \mu$$

$$2*cdf(2*\mu-z) \text{ if } z < \mu \qquad \text{Eq. 1:}$$

where cdf (z) can be the cumulative distribution function of the normal distribution N.

In some embodiments, the process 300 may include removing candidate family tree with anomaly estimates from consideration. For example, candidate family tree with birth-year probability estimates that fall below a predetermined threshold may be regarded as abnormal and be removed from consideration. In some embodiments, the threshold is the lowest probability that could exist for the relationship to be plausible. The threshold may vary by meiosis level.

In some embodiments, a "one-meiosis-event relationship" or "M1 relationship" corresponds to a parent-child relationship, a "two-meiosis-event relationship" or "M2 relationship" corresponds to a sibling relationship, a "three-meiosis-event relationship" or "M3 relationship" corresponds to half-sibling, grandparent-grandchild, or avuncular relationship, a "four-meiosis-event relationship" or "M4 relationship" corresponds to a first cousin, great grandparent to grandchild, half avuncular, or great avuncular relationship, a "five-meiosis-event relationship" or "M5 relationship" corresponds to a first cousin once removed, half first cousin, or half great avuncular relationship, a "six-meiosis-event relationship" or "M6 relationship" corresponds to a second cousin, first cousin twice removed, or half first cousin once removed relationship, a "seven-meiosis-event relationship" or "M7 relationship" corresponds to a second cousin once removed, half second cousin, first cousin thrice removed, or half first cousin once removed relationship, an "eight-meiosis-event relationship" or "M8 relationship" corresponds to a third cousin, or a second cousin twice removed relationship, and a "nine-meiosis-event relationship" or "M9 relationship" corresponds to a third cousin once removed, or second cousin thrice removed relationship, and so on. This is shown in Table 1 below:

TABLE 1

| Number of Meiosis Events | Abbreviation | Possible Relationships |
|---|---|---|
| One-meiosis-event relationship | M1 | Parent-child |
| Two-meiosis-event relationship | M2 | Full Siblings |
| Three-meiosis-event relationship | M3 | Half-siblings, Grandparent, Avuncular |
| Four-meiosis-event relationship | M4 | First cousin, great grandparent, half avuncular |
| Five-meiosis-event relationship | M5 | First cousin once removed, half first cousin, great-great avuncular, great-great grandparent |
| Six-meiosis-event relationship | M6 | Second cousin, first cousin twice removed, half first cousin once removed, half two-generation avuncular, three-generation grandparent |
| Seven-meiosis event relationship | M7 | Second cousin once removed, half second cousin, first cousin thrice removed, half first cousin twice removed, four-generation avuncular, half three-generation avuncular, four-generation grandparent |

TABLE 1-continued

| Number of Meiosis Events | Abbreviation | Possible Relationships |
| --- | --- | --- |
| Eight-meiosis event relationship | M8 | Third cousin, second cousin twice removed, half second cousin once removed, first cousin four times removed, half first cousin three times removed, five-generation avuncular, half four-generation avuncular, five-generation grandparent |
| Nine-meiosis event relationship | M9 | Third cousin once removed, half third cousin, second third cousin thrice removed, half second cousin twice removed, first cousin five times removed, half first cousin four times removed, six-generation avuncular, half five-generation avuncular |
| Ten-meiosis-event relationship | M10 | Fourth cousin, third cousin twice removed, half third cousin once removed, second cousin four times removed, half second cousin thrice removed, first cousin six times removed, half first cousin five times removed, seven-generation avuncular, half six-generation avuncular |

In some embodiments, for one-meiosis-event relationships and two-meiosis-event relationships, a birth-year probability cutoff threshold of 0.01 is used. In some embodiments, a threshold of 0.1 is used for three-meiosis-event relationships through six-meiosis-event relationships.

In some embodiments, the process 300 may include removing duplicates from consideration, e.g., those candidate family trees with the same genetic likelihood and the same birth-year probability. The family trees with the same genetic likelihood and the same birth-year probability may be determined to be having the same proposed placement.

With continued reference to FIG. 3, the process 300 can additionally include a step 360 of sorting candidate family trees by genetic probability and birth-year probability. In some embodiments, the candidate family trees may be first sorted by genetic probability. According to some embodiments, if the genetic probabilities are the same or within a similarity threshold, such candidate family trees are further sorted by birth-year probability.

The process 300 may also include determining a confidence level for each candidate family tree. For example, for one-meiosis-event relationships and two-meiosis-event relationships, a top estimate determined by the combined genetic and birth-year probabilities is deemed "high confidence." In some embodiments, for three-meiosis-event relationships and four-meiosis-event relationships, a combined probability of greater than or equal to 1.5 is deemed "high confidence" while 1.0-1.5 is deemed "medium confidence" and less than 1.0 is "low confidence." In some embodiments, for five-meiosis-event relationships and more distance relationships, a probability of greater than 0.5 is deemed "medium confidence" with less than 0.5 deemed "low confidence."

With continued reference to FIG. 3, the process 300 can additionally include a step 370 of selecting one of the candidate family trees as a proposed family tree. In some embodiments, one or more candidate family trees may be selected as proposed family trees and are presented to a user to confirm the proposed relationships or perform further evaluation. For example, the result of the process 300 may be presented by the tree management engine 260 via a graphical user interface in the process of helping a user to build a family tree.

As seen in Table 2 below, the accuracy of using process 300 at different meiosis levels is shown. Accuracy is defined as the percentage of generated candidate family trees that agree with known information from the stitched tree database. Top-result accuracy is the percentage of samples wherein the top-ranked candidate family trees agrees with the stitched tree database, and top-three accuracy is the percentage of samples wherein at least one of the top three estimated candidate family trees agrees with the stitched tree database.

TABLE 2

| Meiosis Events | Birth-year probability Cutoff | Previous Top-Result Accuracy | New Top-Result Accuracy | Top-Three Accuracy |
| --- | --- | --- | --- | --- |
| 1 | 0.01 | 49.3% | 93.64% | 96.33% |
| 2 | 0.01 | 95% | 95.27% | 96.43% |
| 3 | 0.1 | 43% | 69.85% | 83.05% |
| 4 | 0.1 | 41% | 72.55% | 91.83% |
| 5 | 0.1 | 24% | 58.29% | 88.79% |
| 6 | 0.1 | 27% | 50.04% | 86.23% |

As seen above, the use of birth-year probability substantially improves one-meiosis-event relationships and three-meiosis-event and six-meiosis-event relationships, with a surprising 20-30+% boost in accuracy for many levels. A substantial boost to two-meiosis-event-relationships is not observed because of the relative ease with which two-meiosis-event relationships can be resolved without birth-year information.

Figure 5A:
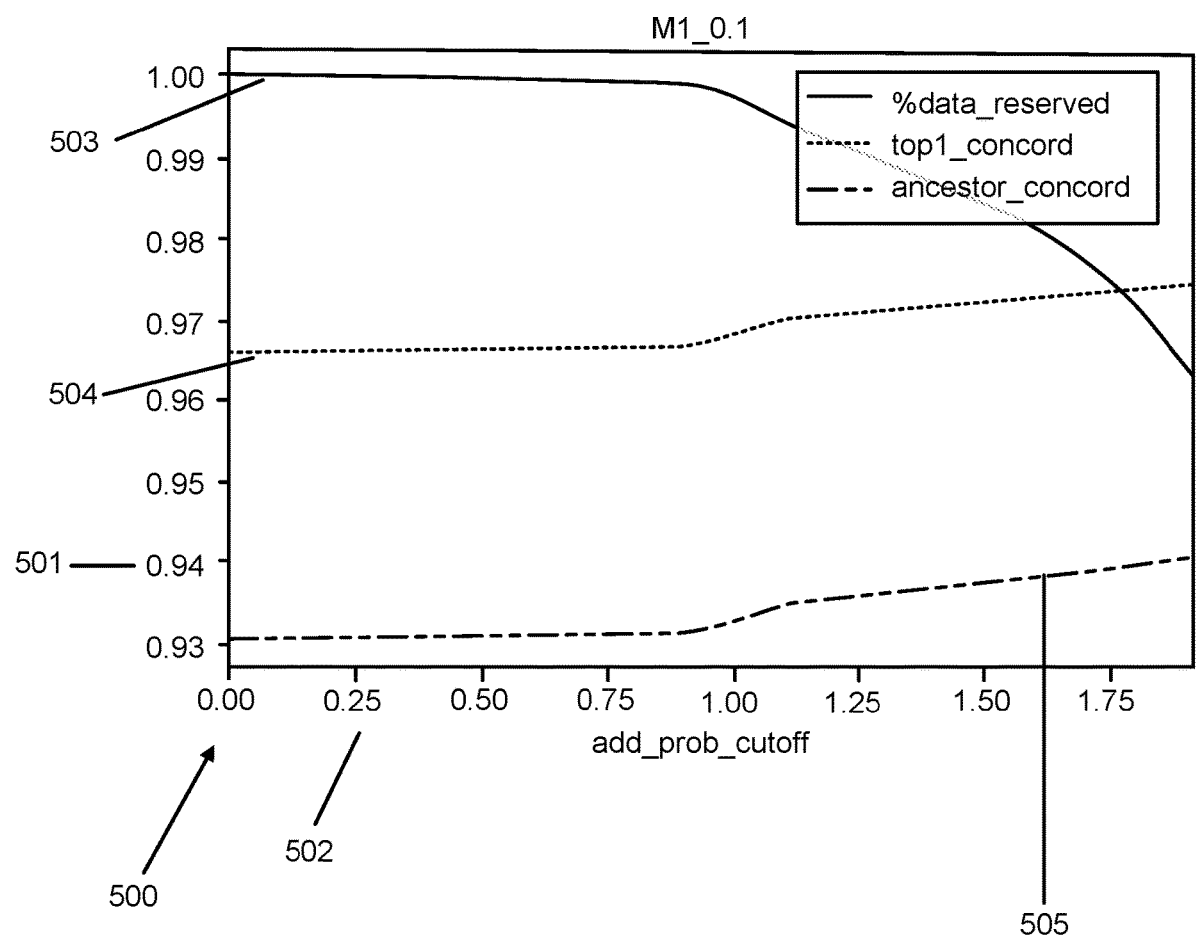
FIG. 5A is graph of results of the scoring method according to an embodiment of the disclosure for one-meiosis-event relationships.

Turning to FIG. 5A, a graph 500 of results from the disclosed embodiments is shown. The graph 500 shows accuracy 501 against a probability level 502 at a birth-year probability cutoff of 0.1, tracking a top estimate 505 (meaning accuracy on right generation plus right ancestor per benchmarking against a stitched tree database), an ancestor concordance value 504 (indicating the correct ancestor was identified but incorrect generation per benchmarking against the stitched tree database), and a percentage of data reserved 503 (e.g., by anomaly removal). As data are removed by high thresholds for probability, higher accuracy comes at the expense of certain accurate results that are removed until very few data, e.g., a few candidate family trees, are retained.

As seen, as the total probability hits 1.5, accuracy of the top estimate 505 reaches a sufficiently high level, e.g., approximately 94% agreement with confirmed genealogical relationships.

Figure 5B:
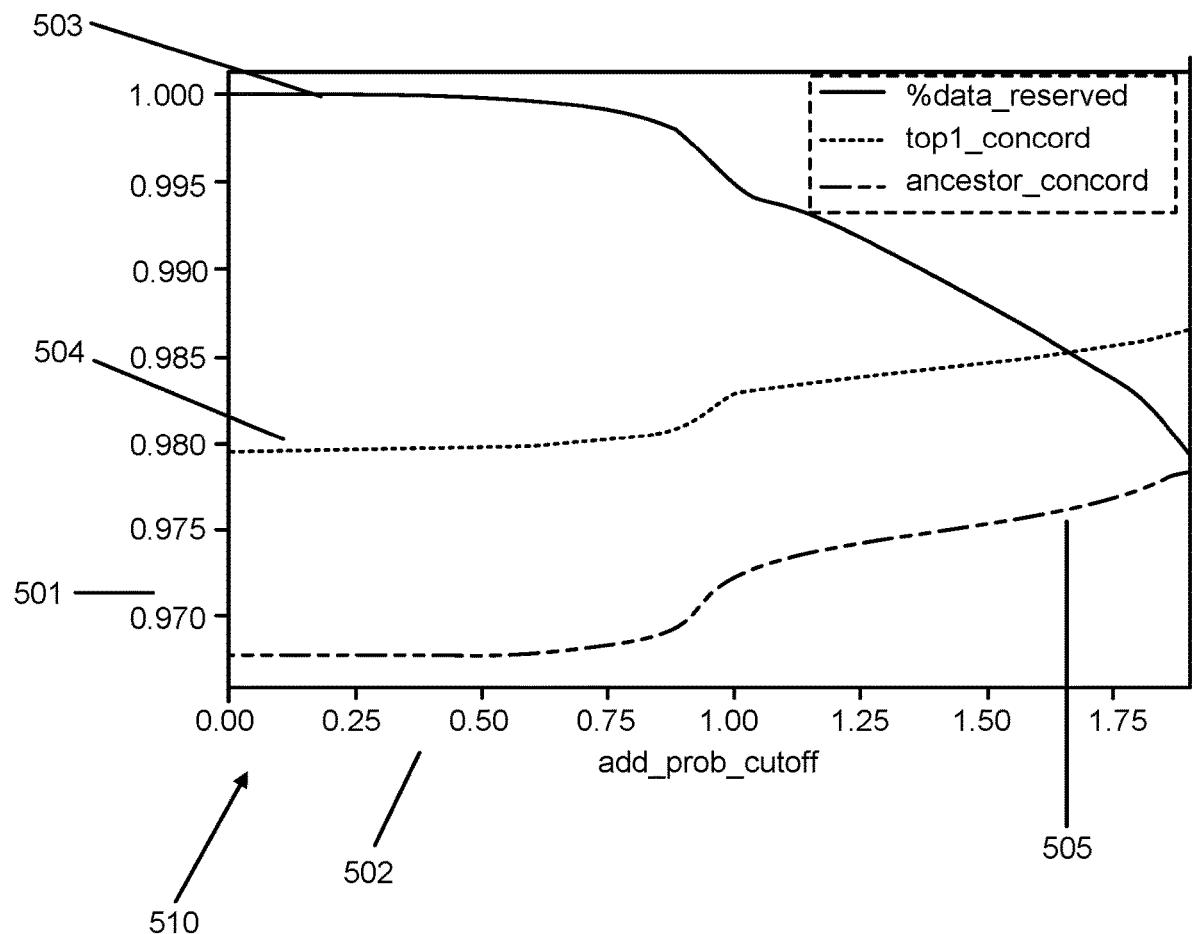
FIG. 5B is a graph of results of the scoring method according to the embodiment of FIG. 5A for two-meiosis-event relationships.

FIG. 5B shows a graph 510 wherein M2 relationships are tracked at a birth-year probability cutoff of 0.1. Similarly, as the combined genetic probability and birth-year probability increases past 1.5, very high accuracy—over 97%—is achieved.

Figure 5C:
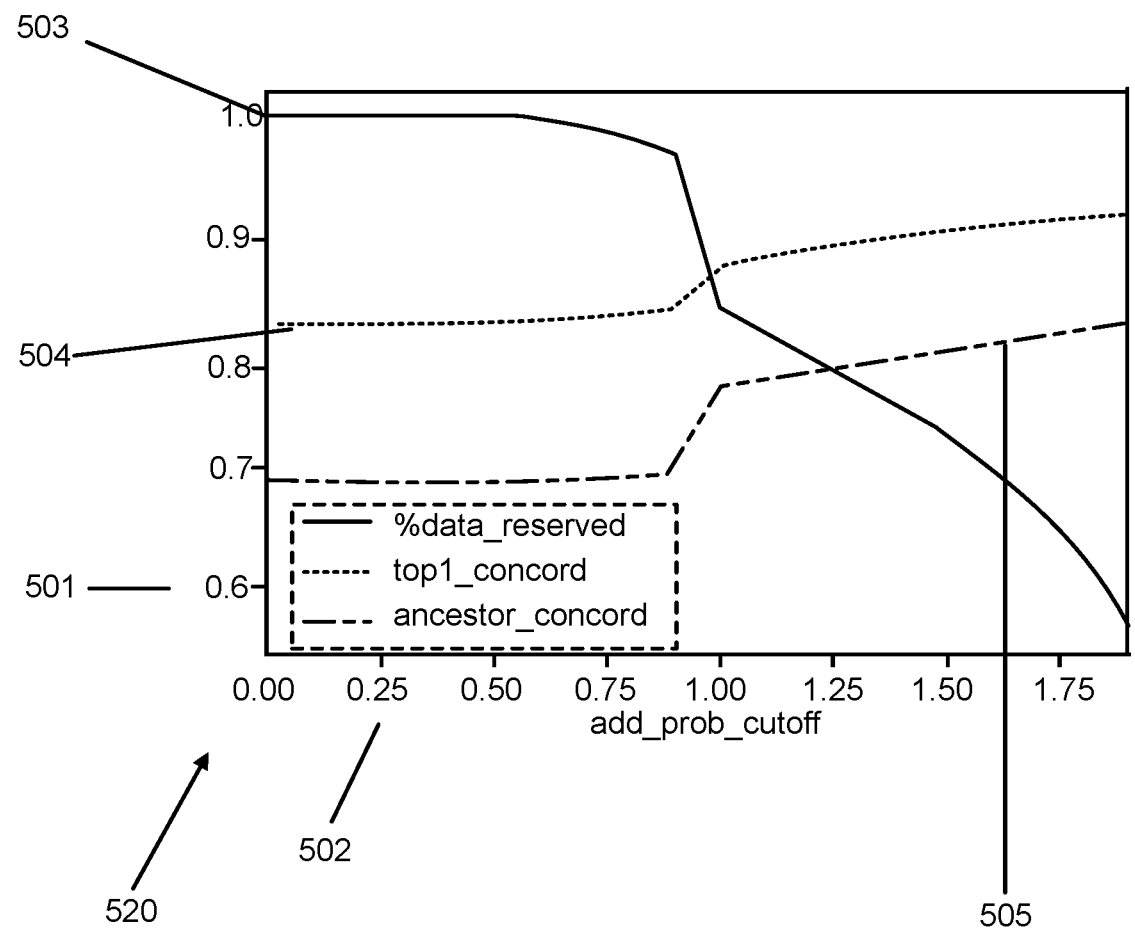
FIG. 5C is a graph of results of the scoring method according to the embodiment of FIG. 5A for three-meiosis-event relationships.
Figure 5D:
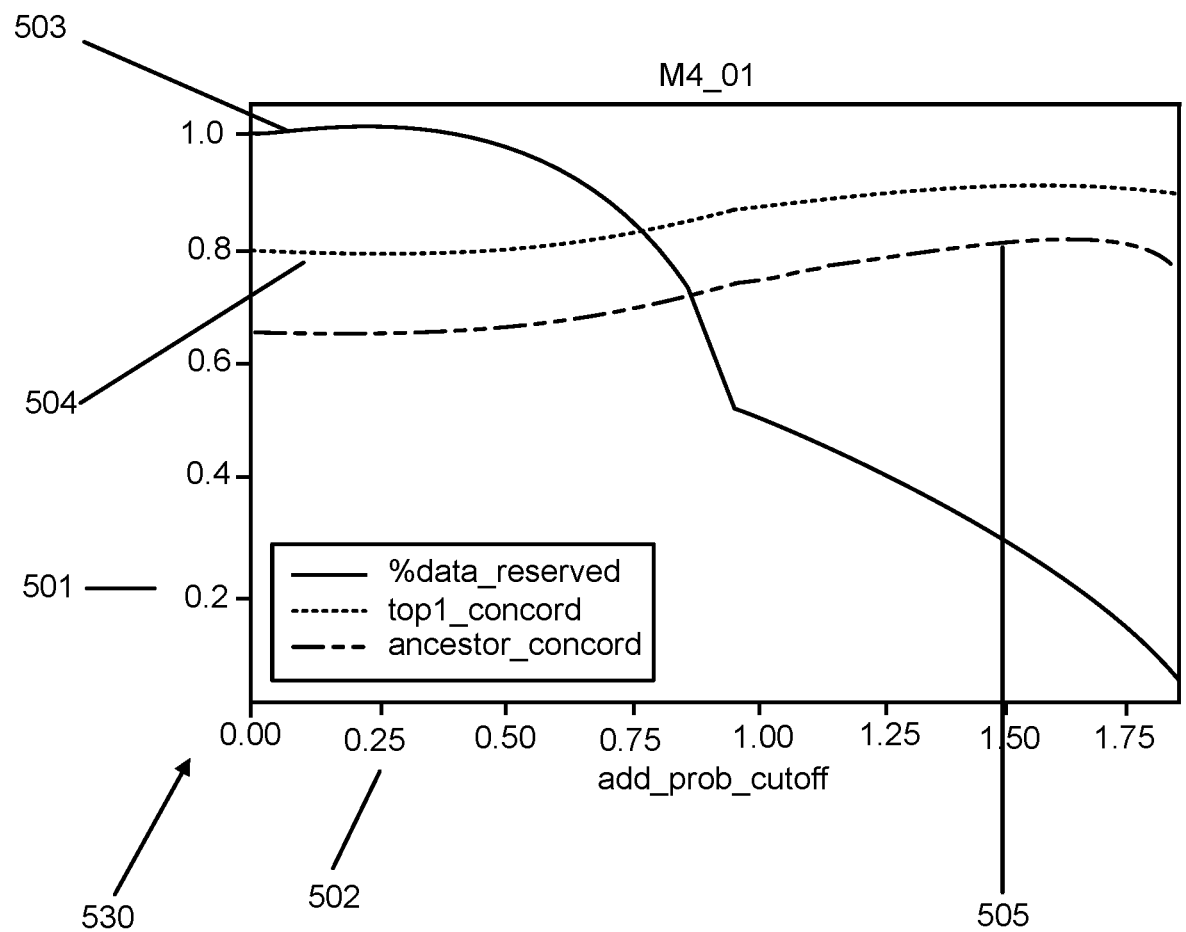
FIG. 5D is a graph of results of the scoring method according to the embodiment of FIG. 5A for four-meiosis-event relationships.

FIG. 5C shows a graph 520 wherein a birth-year probability cutoff of 0.1 is used for M3 relationships. As seen, the accuracy for a top estimate 505 increases substantially at a combined probability of 1.0, such that medium confidence can be given to estimates between 1.0 and 1.5 and high confidence above 1.5 (approximately 80%). A similar pattern is observable in the graph 530 of FIG. 5D, corresponding to M4 relationships at a birth-year probability cutoff of 0.1.

Figure 5E:
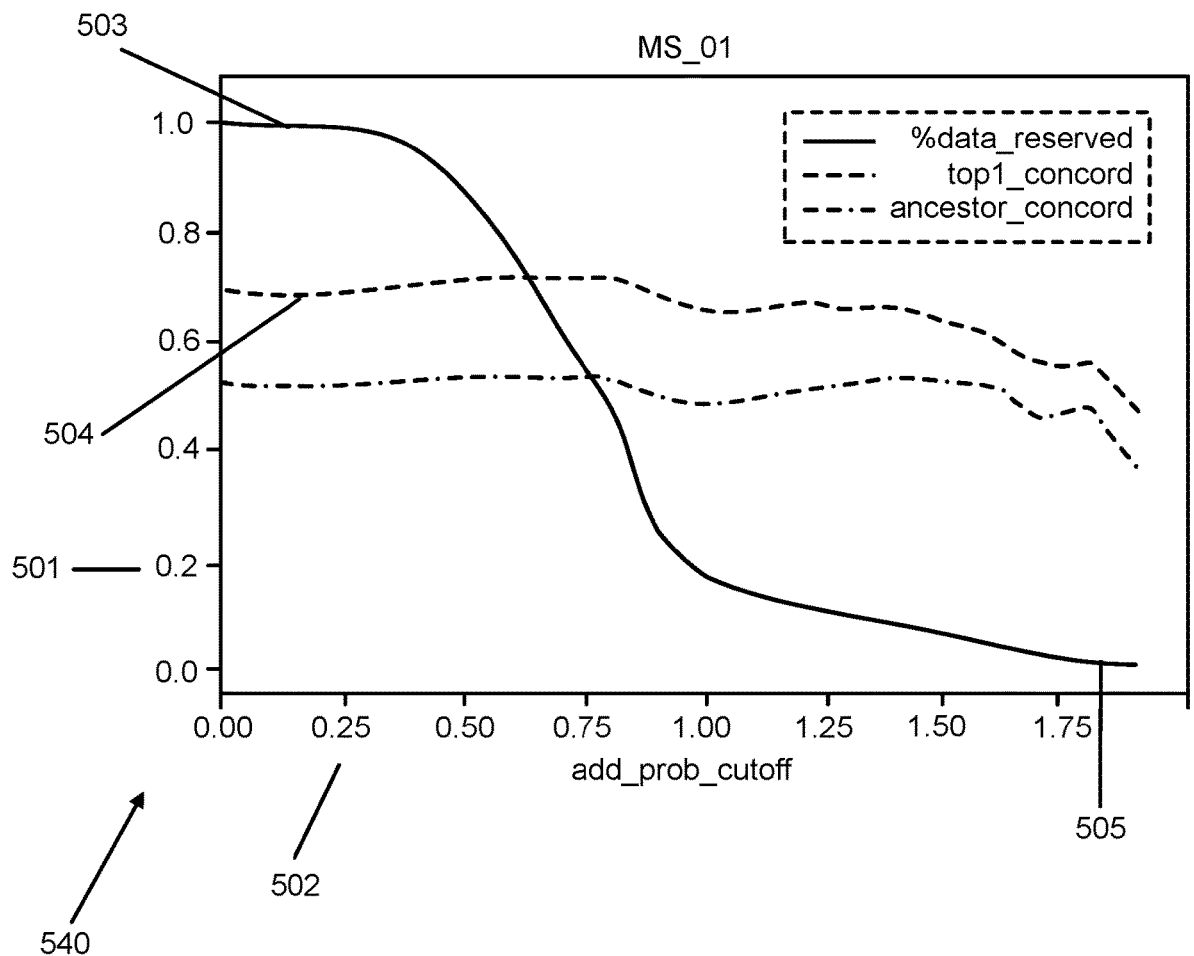
FIG. 5E is a graph of results of the scoring method according to the embodiment of FIG. 5A for five-meiosis-event
Figure 5F:
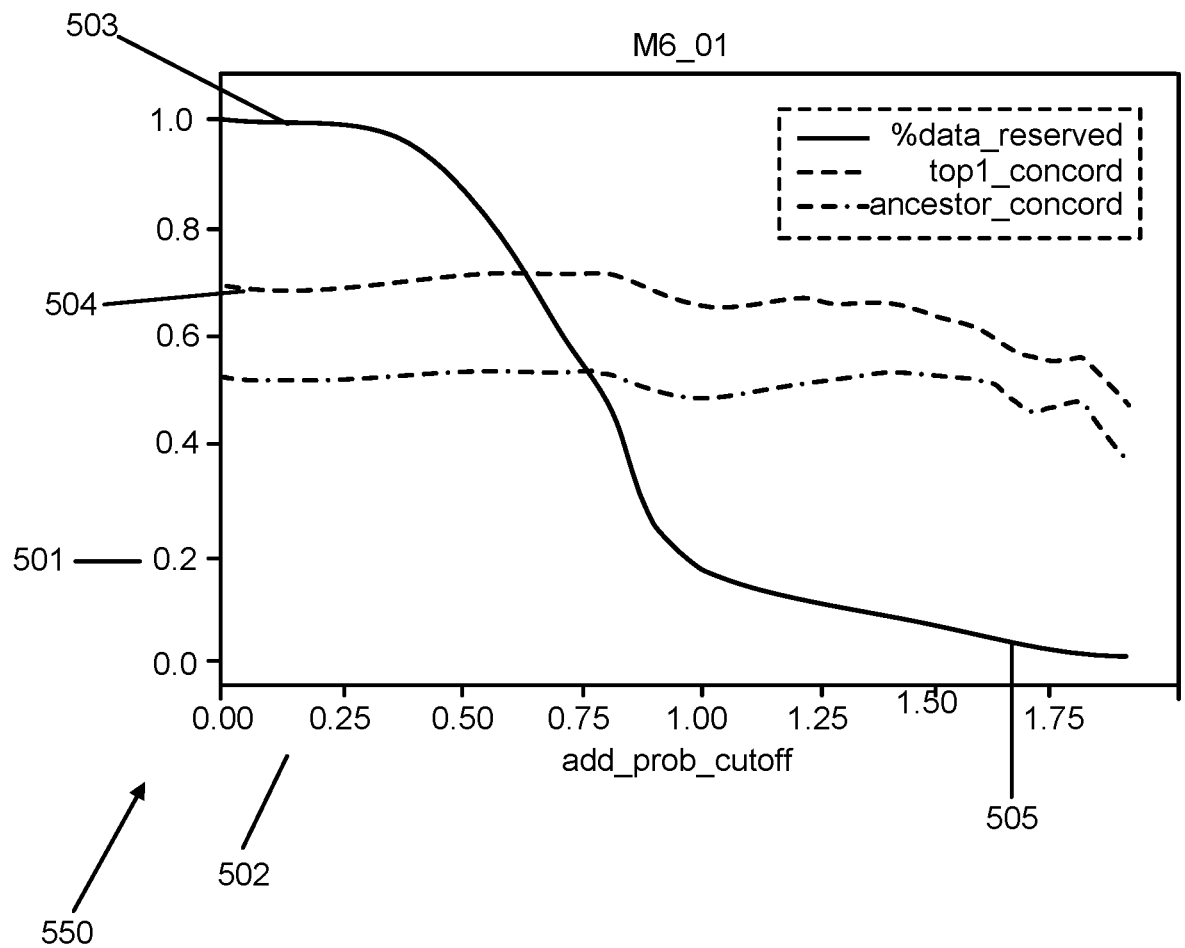
FIG. 5F is a graph of results of the scoring method according to the embodiment of FIG. 5A for six-meiosis-event relationships.

FIG. 5E shows a graph 540 of M5 relationships at a birth-year probability cutoff of 0.1. As seen, the accuracy above 0.5 combined probability is static at about 55%, such that medium confidence is given above 0.5. Likewise, FIG. 5F shows a graph 550 in which accuracy does not substantially increase above a combined probability of 0.5.

Figure 6A:
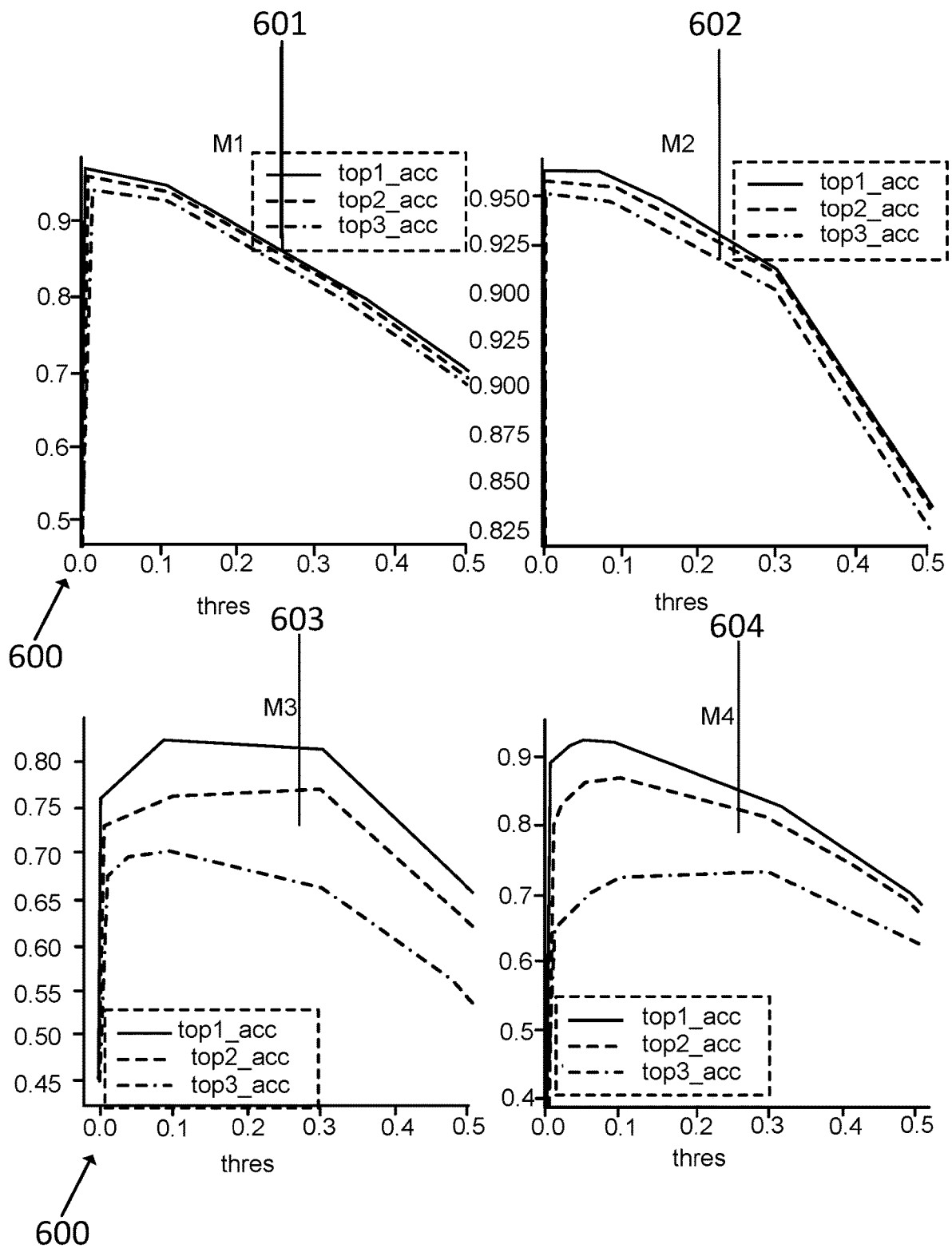
FIG. 6A is a graph of plots of the scoring method for one-meiosis-event relationships through eight-meiosis-event relationships according to an embodiment of the disclosure.
Figure 6B:
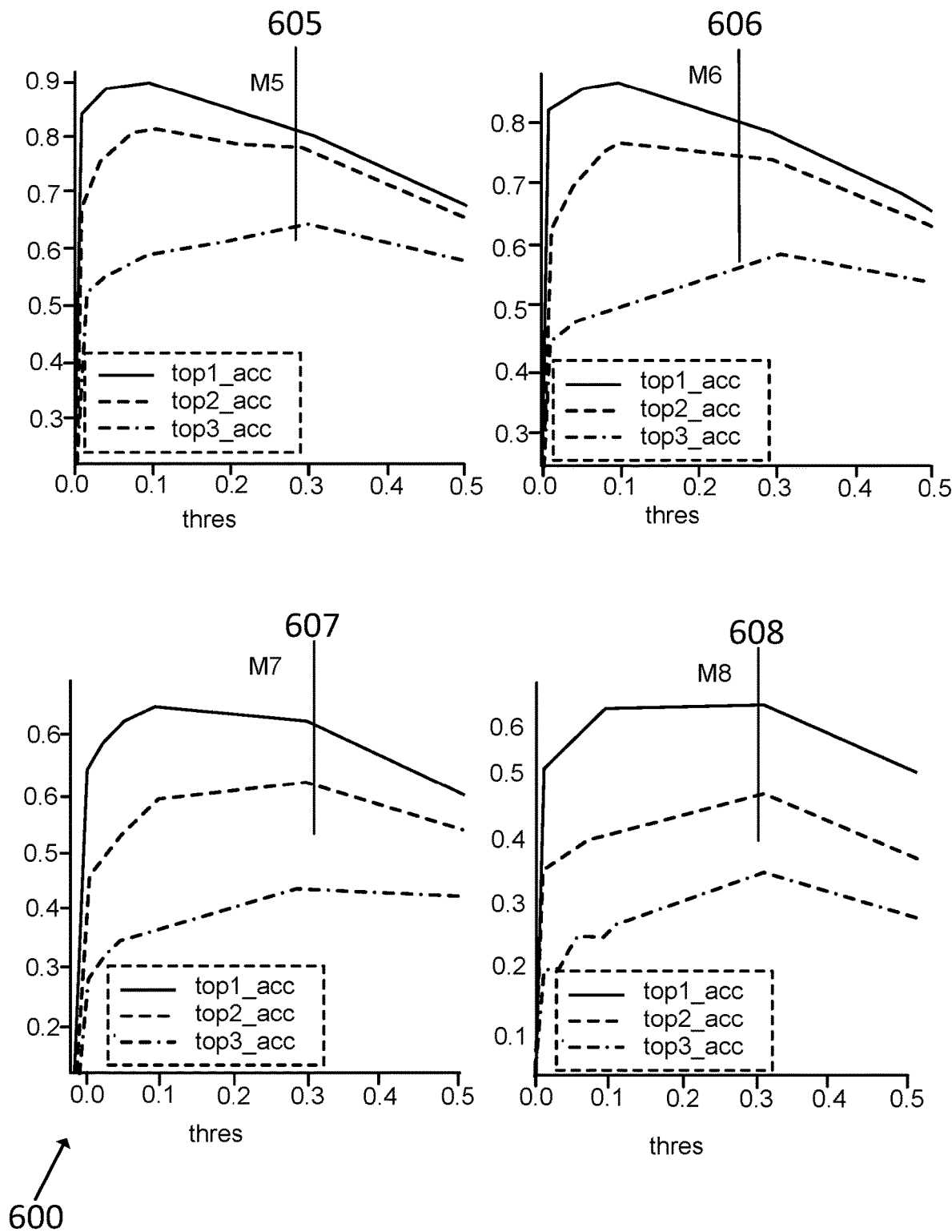
FIG. 6B is a diagram of a method according to an embodiment of the present disclosure.

FIGS. 6A and 6B show charts 600 of plots 601, 602, 603, 604, 605, 606, 607, 608 corresponding respectively to one-meiosis-event relationships through eight-meiosis-event relationships. As seen, the plots 601, 602, 603, 604, 605, 606, 607, 608 illustrate the top result, top two results, and top three results accuracy against a birth-year cutoff threshold, ranging from 0.0 to 0.5. With one-meiosis-event relationships 601 and two-meiosis-event relationships 602, the accuracy is high at 0.01 cutoff threshold; with three-meiosis-event relationships 603 through eight-meiosis-event relationships 608, the accuracy are highest at 0.1 threshold and decrease therefrom. Accordingly, different birth-year probability cutoffs are used for one-meiosis-event relationships and two-meiosis-event relationships vs. three-meiosis-event relationships through eight-meiosis-event relationships.

This is borne out by the data shown in Table 3 below, where the accuracy and confidence levels at different cut offs are shown. Accuracy, here, refers to a correct relationship prediction and the right ancestor, here, refers to the right genetic, MRCA relationship.

TABLE 3

| Relationship | Birth-Year Probability Cutoff | Number of Results | Results |
| --- | --- | --- | --- |
| One meiosis event | 0.01 | Top 1 | High confidence (99%) |
| Two meiosis events | 0.01 | Top 1 | High Confidence (99%) |
| Three meiosis events | 0.1 | Top 3 | High (1.5): 80% accuracy, 90% right ancestor Medium (1.0): 55% accuracy, 70% right ancestor Low (0.0): 25% accuracy, 55% right ancestor |
| Four meiosis events | 0.1 | Top 3 | High (1.5): 80% accuracy, 90% right ancestor Medium (1.0): 65% accuracy, 80% right ancestor Low (0.0): 25% accuracy, 55% right ancestor |
| Five meiosis events | 0.1 | Top 3 | Medium (0.5): 54% accuracy, 70% right ancestor Low (0.0): 40% accuracy, 51% right ancestor |
| Six meiosis events | 0.1 | Top 3 | Medium (0.5): 49% accuracy, 69% right ancestor Low (0.0): 35% accuracy, 51% right ancestor |

As seen, the use of the birth-year probability cutoff, tailored to relationship level, advantageously maximizes accuracy and ancestor determination, even at highly attenuated relationships like six-meiosis-event relationships. This is performed while minimizing the number of candidate family trees that are discarded, as these may contain accurate relationships and information. Further, accuracy improvements and performance gains are simultaneously realized using the embodiments of the disclosure.

The impact of the birth-year probability cutoff is shown below in Table 4, where the accuracy before and after using the birth-year probability cutoff are compared.

TABLE 4

| Relationship | Birth-Year Probability Cutoff | Before | After |
| --- | --- | --- | --- |
| One meiosis event | 0.01 | 49.3% | 92.5% |
| Two meiosis events | 0.01 | 95% | 95% |
| Three meiosis events | 0.1 | 43% | 66% |
| Four meiosis events | 0.1 | 41% | 60% |
| Five meiosis events | 0.1 | 24% | 37% |
| Six meiosis events | 0.1 | 27% | 37% |

As seen, accuracy improved substantially by using a birth-year probability cutoff as determined in part by the plots of FIG. 6. As two-meiosis-event relationships are easier to resolve, the improvement was primarily observed in one-meiosis-event relationships, three-meiosis-event relationships, and higher meiosis relationships.

The disclosed embodiments advantageously allow for balancing the accuracy of a genetic-match determination and family tree generation process while preserving data by using birth year data to augment findings based on genetic inferences. Thus, the risk of pruning correct estimates (e.g., correctly generated candidate family trees) is minimized. This is facilitated by normalizing genetic and birth-year probabilities. Birth-year probabilities may be determined by utilizing a normal distribution of birth years and a determined number of generations separating a target and match person from a MRCA. This process advantageously improves the accuracy of predictions without sacrificing data, as compared against a benchmark of a stitched tree database or other ground truth data.

In some embodiments, anomaly estimates are removed and the genetic likelihood is converted to probability to infer the correct candidate family tree. In other embodiments, a new likelihood based on the genetic likelihood and a birth-year likelihood, for example the genetic likelihood multiplied by the birth-year likelihood, is determined and then used to rank candidate family trees. In yet other embodiments, anomaly estimates are removed, genetic likelihood is converted to genetic probability, the candidate family trees are collapsed and ranked by order of genetic probability then birth-year probability, then the resulting probabilities are categorized and labeled as high confidence, medium confidence, or low confidence.

Computing Machine Architecture

Figure 7:
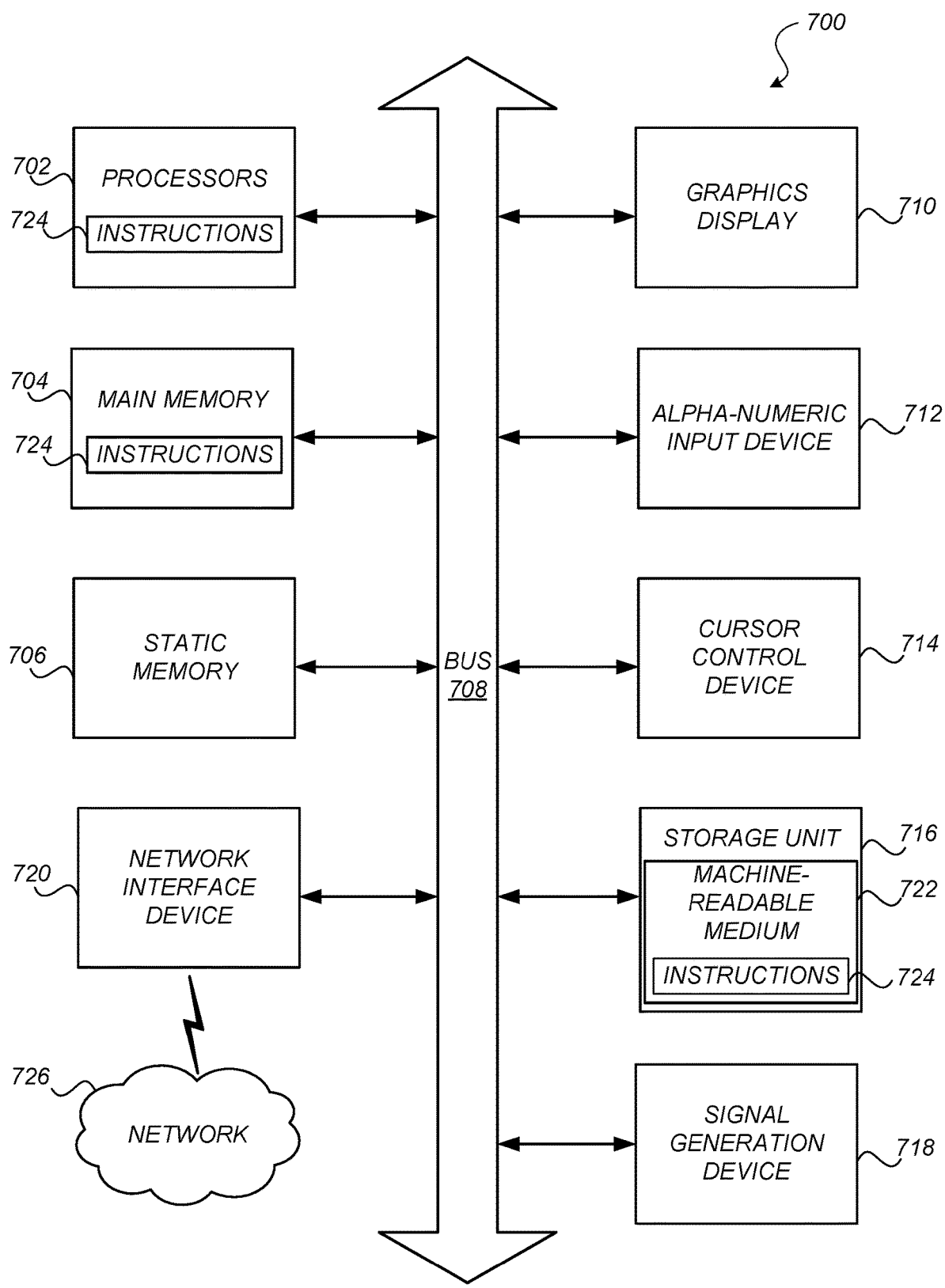
FIG. 7 is a block diagram of an example computing device, in accordance with some embodiments.

FIG. 7 is a block diagram illustrating components of an example computing machine that is capable of reading instructions from a computer-readable medium and execute them in a processor (or controller). A computer described herein may include a single computing machine shown in FIG. 7, a virtual machine, a distributed computing system that includes multiple nodes of computing machines shown in FIG. 7, or any other suitable arrangement of computing devices.

By way of example, FIG. 7 shows a diagrammatic representation of a computing machine in the example form of a computer system 700 within which instructions 724 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 7 may correspond to any software, hardware, or combined components shown in FIGS. 1 and 2, including but not limited to, the client device 110, the computing server 130, and various engines, interfaces, terminals, and machines shown in FIG. 2. While FIG. 7 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 724 that specify actions to be taken by that machine. Further, while only a single machine is illustrated, the term "machine" and "computer" may also be taken to include any collection of machines that individually or jointly execute instructions 724 to perform any one or more of the methodologies discussed herein.

The example computer system 700 includes one or more processors 702 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 700 may also include a memory 704 that store computer code including instructions 724 that may cause the processors 702 to perform certain actions when the instructions are executed, directly or indirectly by the processors 702. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 702 and reduces the space required for the memory 704. For example, the data processing techniques and machine learning methods described herein reduce the complexity of the computation of the processors 702 by applying one or more novel techniques that simplify the steps in determining likelihoods and probabilities, training, reaching convergence, and generating results of the processors 702. The algorithms described herein also reduces the size of the models and datasets to reduce the storage space requirement for memory 704.

The performance of certain operations may be distributed among more than one processor, not only residing within a single machine, but deployed across a number of machines. In some example embodiments, the one or more processors or processor-implemented modules may be located in a single geographic location (e.g., within a home environment, an office environment, or a server farm). In other example embodiments, one or more processors or processor-implemented modules may be distributed across a number of geographic locations. Even though in the specification or the claims may refer some processes to be performed by a processor, this should be construed to include a joint operation of multiple distributed processors.

The computer system 700 may include a main memory 704, and a static memory 706, which are configured to communicate with each other via a bus 708. The computer system 700 may further include a graphics display unit 710 (e.g., a plasma display panel (PDP), a liquid crystal display (LCD), a projector, or a cathode ray tube (CRT)). The graphics display unit 710, controlled by the processors 702, displays a graphical user interface (GUI) to display one or more results and data generated by the processes described herein. The computer system 700 may also include alphanumeric input device 712 (e.g., a keyboard), a cursor control device 714 (e.g., a mouse, a trackball, a joystick, a motion sensor, or other pointing instruments), a storage unit 716 (a hard drive, a solid-state drive, a hybrid drive, a memory disk, etc.), a signal generation device 718 (e.g., a speaker), and a network interface device 720, which also are configured to communicate via the bus 708.

The storage unit 716 includes a computer-readable medium 722 on which is stored instructions 724 embodying any one or more of the methodologies or functions described herein. The instructions 724 may also reside, completely or at least partially, within the main memory 704 or within the processor 702 (e.g., within a processor's cache memory) during execution thereof by the computer system 700, the main memory 704 and the processor 702 also constituting computer-readable media. The instructions 724 may be transmitted or received over a network 726 via the network interface device 720.

While computer-readable medium 722 is shown in an example embodiment to be a single medium, the term "computer-readable medium" should be taken to include a single medium or multiple media (e.g., a centralized or distributed database, or associated caches and servers) able to store instructions (e.g., instructions 724). The computer-readable medium may include any medium that is capable of storing instructions (e.g., instructions 724) for execution by the processors (e.g., processors 702) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g.

computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed in the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. Pat. No. 10,679,729, entitled "Haplotype Phasing Models," granted on Jun. 9, 2020, (2) U.S. Pat. No. 10,223,498, entitled "Discovering Population Structure from Patterns of Identity-By-Descent," granted on Mar. 5, 2019, (3) U.S. Pat. No. 10,720,229, entitled "Reducing Error in Predicted Genetic Relationships," granted on Jul. 21, 2020, (4) U.S. Pat. No. 10,558,930, entitled "Local Genetic Ethnicity Determination System," granted on Feb. 11, 2020, (5) U.S. Pat. No. 10,114,922, entitled "Identifying Ancestral Relationships Using a Continuous Stream of Input," granted on Oct. 30, 2018, (6) U.S. Patent Publication Application No., entitled "Linking Individual Datasets to a Database," US2021/0216556, published on Jul. 15, 2021, (7) U.S. Pat. No. 10,692,587, entitled "Global Ancestry Determination System," granted on Jun. 23, 2020, and (8) U.S. Patent Application Publication No. US 2021/0034647, entitled "Clustering of Matched Segments to Determine Linkage of Dataset in a Database," published on Feb. 4, 2021.

What is claimed is:

1. A computer-implemented method, comprising:
identifying a candidate matching individual using genetic data from a target individual wherein identifying the candidate matching individual comprises identifying a first set of identity-by-descent (IBD) segments shared between the target individual and the candidate matching individual;
generating a plurality of candidate family trees based on the genetic data of a target individual and a known family tree of the candidate matching individual, each candidate family tree having a proposed placement of the target individual within the candidate family tree;
determining, for each candidate family tree, a genetic likelihood associated with the candidate family tree as depicted by the proposed placement, wherein the genetic likelihood corresponds to a likelihood of a proposed relationship depicted by the proposed placement as opposed to alternative relationships, wherein determining, for each candidate family tree, the genetic likelihood associated with the candidate family tree as depicted by the proposed placement comprises:
identifying an additional family member in the candidate family tree, the additional family member having genetic data available and being different from the candidate matching individual,
determining a second set of IBD segments shared between the target individual and the additional family member,
determining a likelihood of the proposed placement based on the second set of IBD segments;
determining a most recent common ancestor (MRCA) for the target individual and the matching individual;

determining, for each candidate family tree, a birth-year probability based on a first number of generations between the target individual and the MRCA and a second number of generations between the matching individual and the MRCA to evaluate the candidate family tree, wherein the birth-year probability is based on a number of years between the target individual and the matching individual and a normal distribution of ages for parent-child age differences in a population;

sorting the plurality of candidate family trees based on the genetic likelihood and the birth-year probability in each candidate family tree; and selecting one of the candidate family trees as a proposed family tree.

2. The computer-implemented method of claim 1, further comprising:
removing one or more of the candidate family trees as candidates, wherein the removed candidate family trees are each associated with a value of the birth-year probability that is below a threshold.

3. The computer-implemented method of claim 2, wherein the threshold is 0.01 for one-meiosis-event relationships and two-meiosis-event relationships in order for the one-meiosis-event relationship and the two-meiosis-event relationship to be possible.

4. The computer-implemented method of claim 2, wherein the threshold is 0.1 for three-meiosis-event relationships and more-distant relationships in order for the three-meiosis-event relationships and the more-distant relationships to be possible.

5. The computer-implemented method of claim 1, further comprising:
removing one or more of the candidate family trees as candidates, wherein the removed candidate family trees are associated with duplicate estimates that have equal genetic likelihoods and birth-year probabilities.

6. The computer-implemented method of claim 1, wherein sorting the plurality of candidate family trees is based on the birth-year probability if the genetic probabilities of two candidate family trees are within a similarity threshold.

7. The computer-implemented method of claim 1, wherein sorting the plurality of candidate family trees is first based on genetic likelihoods associated with the plurality of candidate family trees and, secondarily, the birth-year probabilities of the proposed relationships associated with the plurality of candidate family trees.

8. The computer-implemented method of claim 1, wherein the genetic likelihood is converted to the genetic probability using a logarithmic transformation of the form:

$$p_1 = \frac{e^{x1}}{e^{x1} + e^{x2} + \ldots}$$

9. The computer-implemented method of claim 1, wherein sorting the plurality of candidate family trees comprises:
determining, for each candidate family tree, a confidence level for the candidate family tree being a correct family tree, wherein the confidence level is determined by summing the birth-year probability and the genetic likelihood; and
using the confidence level for each candidate family tree to sort the candidate family trees.

10. The computer-implemented method of claim 9, wherein the determined confidence level is considered high confidence for a candidate family tree that is associated with a one-meiosis-event relationship if the determined confidence level is the highest determined confidence out of determined confidences of the plurality of candidate family trees.

11. The computer-implemented method of claim 1, wherein determining the birth-year probability comprises:
determining an age difference z between the target individual and the matching individual;
determining the first number of generations between the target individual and the MRCA;
determining the second number of generations between the matching individual and the MRCA;
determining the birth-year probability by determining a cumulative distribution function of the age difference z given the first and second numbers of generations.

12. The computer-implemented method of claim 11, wherein the cumulative distribution function is defined as the age difference z following a relationship N, wherein N is the mean age difference p multiplied by the number of generations between the target individual and the MRCA, minus the number of generations between the matching individual and the MRCA, and the standard deviation of the age difference σ is multiplied by the square root of the number of generations between the target individual and the MRCA added to the number of generations between the matching individual and the MRCA, according to:

$$2*cdf(z) \text{ if } z \leq \mu$$

$$2(cdf(2*(\mu-z)) \text{ if } z < \mu$$

13. A system comprising one or more processors and one or more hardware storage devices having stored thereon computer-executable instructions that, when executed by the one or more processors, causes the one or more processors to:
identify a candidate matching individual using genetic data from a target individual, wherein identifying the candidate matching individual comprises identifying a first set of identity-by-descent (IBD) segments shared between the target individual and the candidate matching individual;
generate a plurality of candidate family trees based on the genetic data of a target individual and a known family tree of the candidate matching individual, each candidate family tree having a proposed placement of the target individual within the candidate family tree;
determine, for each candidate family tree, a genetic likelihood associated with the candidate family tree as depicted by the proposed placement, wherein the genetic likelihood corresponds to a likelihood of a proposed relationship depicted by the proposed placement as opposed to alternative relationships, wherein determining, for each candidate family tree, the genetic likelihood associated with the candidate family tree as depicted by the proposed placement comprises:
identifying an additional family member in the candidate family tree, the additional family member having genetic data available and being different from the candidate matching individual,
determining a second set of IBD segments shared between the target individual and the additional family member,
determining a likelihood of the proposed placement based on the second set of IBD segments;

determine a most recent common ancestor (MRCA) for the target individual and the matching individual;

determine, for each candidate family tree, a birth-year probability based on a first number of generations between the target individual and the MRCA and a second number of generations between the matching individual and the MRCA to evaluate the candidate family tree, wherein the birth-year probability is based on a number of years between the target individual and the matching individual and a normal distribution of ages for parent-child age differences in a population;

sort the plurality of candidate family trees based on the genetic likelihood and the birth-year probability in each candidate family tree; and select one of the candidate family trees as a proposed family tree.

14. The system of claim 13, further configured to perform at least the following:

remove one or more of the candidate family trees as candidates, wherein the removed candidate family trees are each associated with a value of the birth-year probability that is below a threshold.

15. The system of claim 13, further configured to perform at least the following:

remove one or more of the candidate family trees as candidates, wherein the removed candidate family trees are associated with duplicate estimates that have equal genetic likelihoods and birth-year probabilities.

16. The system of claim 13, wherein sorting the plurality of candidate family trees comprises:

determining, for each candidate family tree, a confidence level for the candidate family tree being a correct family tree, wherein the confidence level is determined by summing the birth-year probability and the genetic likelihood; and using the confidence level for each candidate family tree to sort the candidate family trees.

17. A non-transitory computer-readable medium configured to store code comprising instructions, wherein the instructions, when executed by one or more processors, cause the one or more processors to perform steps comprising:

identifying a candidate matching individual using genetic data from a target individual wherein identifying the candidate matching individual comprises identifying a first set of identity-by-descent (IBD) segments shared between the target individual and the candidate matching individual;

generating a plurality of candidate family trees based on the genetic data of a target individual and a known family tree of the candidate matching individual, each candidate family tree having a proposed placement of the target individual within the candidate family tree;

determining, for each candidate family tree, a genetic likelihood associated with the candidate family tree as depicted by the proposed placement, wherein the genetic likelihood corresponds to a likelihood of a proposed relationship depicted by the proposed placement as opposed to alternative relationships, wherein determining, for each candidate family tree, the genetic likelihood associated with the candidate family tree as depicted by the proposed placement comprises:

identifying an additional family member in the candidate family tree, the additional family member having genetic data available and being different from the candidate matching individual, determining a second set of IBD segments shared between the target individual and the additional family member, determining a likelihood of the proposed placement based on the second set of IBD segments;

determining a most recent common ancestor (MRCA) for the target individual and the matching individual:

determining, for each candidate family tree, a birth-year probability based on a first number of generations between the target individual and the MRCA and a second number of generations between the matching individual and the MRCA to evaluate the candidate family tree, wherein the birth-year probability is based on a number of years between the target individual and the matching individual and a normal distribution of ages for parent-child age differences in a population:

sorting the plurality of candidate family trees based on the genetic likelihood and the birth-year probability in each candidate family tree: and selecting one of the candidate family trees as a proposed family tree.

18. The non-transitory computer-readable medium of claim 17, further comprising:

removing one or more of the candidate family trees as candidates, wherein the removed candidate family trees are each associated with a value of the birth-year probability that is below a threshold.

19. The non-transitory computer-readable medium of claim 17, further comprising:

removing one or more of the candidate family trees as candidates, wherein the removed candidate family trees are associated with duplicate estimates that have equal genetic likelihoods and birth-year probabilities.

20. The non-transitory computer-readable medium of claim 17, wherein sorting the plurality of candidate family trees comprises:

determining, for each candidate family tree, a confidence level for the candidate family tree being a correct family tree, wherein the confidence level is determined by summing the birth-year probability and the genetic likelihood; and using the confidence level for each candidate family tree to sort the candidate family trees.

* * * * *